United States Patent
El Tayer et al.

(10) Patent No.: US 6,235,755 B1
(45) Date of Patent: May 22, 2001

(54) FSH MIMETICS FOR THE TREATMENT OF INFERTILITY

(75) Inventors: Nabil El Tayer, Milton; Adulla Reddy, Norwood, both of MA (US); David Buckler, Mendham, NJ (US); Sharad Magar, Caton, MA (US)

(73) Assignee: Applied Research Systems ARS Holding N.A., Curacao (AN)

( * ) Notice: Subject to any disclaimer, the term of this patent is extended or adjusted under 35 U.S.C. 154(b) by 0 days.

(21) Appl. No.: 09/369,222

(22) Filed: Aug. 5, 1999

Related U.S. Application Data

(60) Provisional application No. 60/095,712, filed on Aug. 7, 1998.

(51) Int. Cl.[7] .............. A61K 31/37; A61K 31/40; A61K 31/404; A61K 31/435; C07D 401/00

(52) U.S. Cl. .............. 514/315; 514/336; 514/359; 514/277; 514/317; 514/320; 514/326; 546/276.7; 548/444; 548/446; 548/517; 548/518

(58) Field of Search ............... 546/276.7; 548/444, 548/446, 517, 518; 514/277, 315, 317, 320, 326, 336, 359

(56) References Cited

U.S. PATENT DOCUMENTS 3,947,569 * 3/1976 Immer et al. .................. 424/9
5,071,823 12/1991 Kolar et al. .................. 514/15

OTHER PUBLICATIONS

Sprengel et al., *Mol. Endocrinol.* 4:525–530 (1990).
Parmentier et al., *Science* 246:1620–1622 (1989).
Cassidenti et al., *Hum. Reprod.* vol. 7, No. 3, pp. 344–348 (1992).
Breckwoldt et al., *Fert. Steril.* vol. 22, No. 7, pp. 451–455 (1971).
Diedrich et al., *Hum. Reprod.* vol. 3, No. 1, pp. 39–44 (1988).
Kelton et al., *Molecular and Cellular Endocrinology*, 89:141–51 (1992).
Dahl et al., *Methods Enzymol.*, 168:414–423 (1989).

* cited by examiner

*Primary Examiner*—Alan L. Rotman
*Assistant Examiner*—Rita Desai
(74) *Attorney, Agent, or Firm*—McDonnell Boehnen Hulbert & Berghoff

(57) ABSTRACT

The present invention provides non-peptidic amino derivatives, their therapeutic use as well as pharmaceutical compositions that possess activity as Follicle Stimulating Hormone (FSH) agonists and are useful in the for treatment of infertility. In particular, the invention provides cyclic and acyclic alpha- and beta-aminocarboxamides, more particularly tetrahydroisoquinolinecarboxamides, piperidinecarboxamides, pyrrolidinecarboxamides, and 2-amino-3-carboxamidopyridine derivatives.

8 Claims, 7 Drawing Sheets

FSH MIMETICS FOR THE TREATMENT OF INFERTILITY

This application claims the benefit of U.S. Provisional Application No. 60/095,712, filed Aug. 7, 1998.

BACKGROUND OF THE INVENTION

1. Field of the Invention

The present invention relates to non-peptidic amino derivatives, their therapeutic use, as well as pharmaceutical compositions comprising these derivatives. In particular, the invention relates to cyclic and acyclic alpha- and beta-aminocarboxamides, more particularly to tetrahydroisoquinolinecarboxamides, piperidinecarboxatnides, pyrrolidinecarboxamides, and 2-amino-3-carboxamidopyridine derivatives. The compounds of the invention possess activity as Follicle Stimulating Hormone (FSH) agonists and are useful in the treatment of infertility.

2. Summary of the Related Art

Annually in the U.S. there are 2.4 million couples experiencing infertility that are potential candidates for treatment. Follicle stimulating hormone, either extracted from urine or produced by recombinant DNA technology, is a parenterally-administered protein product used by specialists for ovulation induction (OI) and for controlled ovarial hyperstimulation (COH). Whereas OI is directed at achieving a single follicle to ovulate, COH is directed at harvesting multiple oocytes for use in various in vitro assisted reproductive technologies (e.g., for in vitro fertilization). Clinical use of preparations containing FSH began in the 1960's.

Follicle stimulating hormone (FSH) is a pituitary-derived heterodimeric glycoprotein hormone that shares structural similarities with luteinizing hormone (LH) and thyroid stimulating hormone (TSH), both of which are also produced in the pituitary gland, and chorionic gonadotropin (CG), which is produced in the placenta. The hormones are relatively large (28–38 kilodaltons) and are composed of a common a subunit non-covalently bound to a distinct β subunit that confers receptor binding specificity.

The cellular receptors for these hormones are known to be members of the G protein-coupled class of membrane-bound receptors, which when activated stimulate an increase in the activity of adenylyl cyclase. This results in an increase in the level of the intracellular second messenger adenosine 3',5'-monophosphate (cAMP), which in turn causes increased steroid synthesis and secretion. Hydropathicity plots of the amino acid sequences of these receptors reveal three general domains: (1) a hydrophilic amino-terminal region, considered to be the amino-terminal extracellular domain, (2) seven hydrophobic segments of membrane-spanning length, considered to be the transmembrane domain, and (3) a carboxy-terminal region that contains potential phosphorylation sites (serine, threonine, and tyrosine residues), considered to be the carboxy-terminal intracellular or cytoplasmic domain. The glycoprotein hormone receptor family is distinguished from other G protein-coupled receptors, such as the β2-adrenergic, rhodopsin, and substance K receptors, by the large size of the hydrophilic amino-terminal domain, which is involved in hormone binding.

The FSH receptor is expressed on testicular Sertoli cells and ovarian granulosa cells. While there has been a recognized need for providing essentially pure human FSH receptor, purification of naturally derived preparations is not practical and would likely be insufficient to permit determination of the amino acid sequence. Recently, one group has cloned the cDNA encoding the rat FSH receptor, deduced the amino acid sequence, and expressed it in mammalian cells (Sprengel, *Mol. Endocrinol.* 4: 525 (1990)). Another group, attempting to clone the TSH receptor, apparently also cloned and identified a portion of the transmembrane region of the human FSH receptor (Parmentier, *Science* 246: 1620 (1989)).

Use of FSH is limited by its high cost, lack of oral dosing, and need of extensive monitoring by specialist physicians. Hence, identification of a non-peptidic small molecule substitute for FSH that could potentially be developed for oral administration is desirable.

SUMMARY OF THE INVENTION

We have now found non-peptidic compounds for the treatment of infertility that mimic the action of FSH. Such compounds have superior convenience of use compared to FSH due to their oral bioavailability. They are suitable for prescription by a Ob/Gyn, require minimal supervision, and have substantially lower costs compared to FSH treatment.

DETAILED DESCRIPTION OF THE INVENTION

Figure 1:
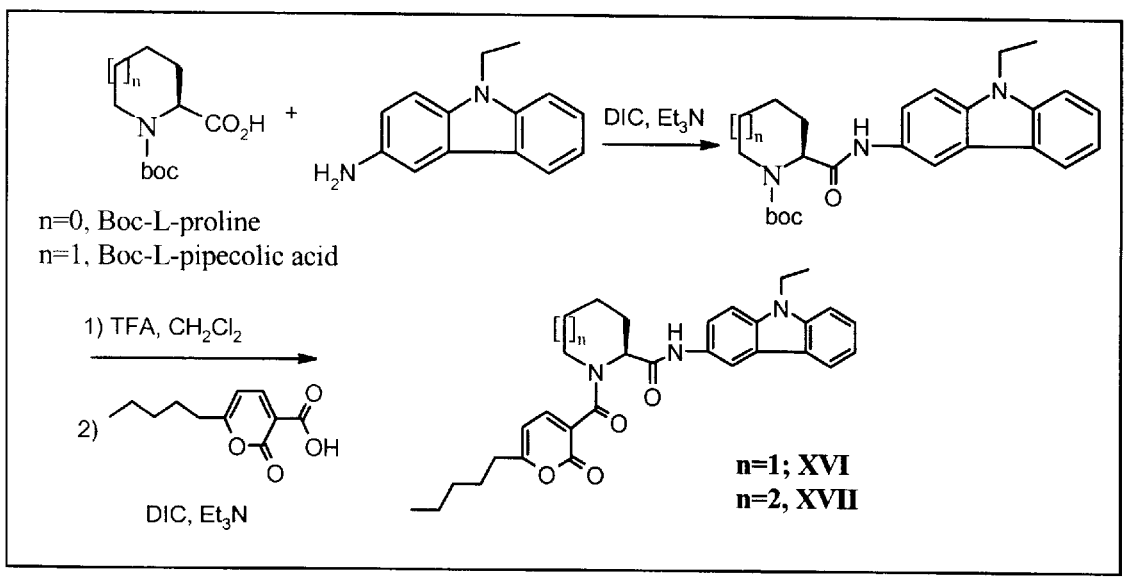
FIG. 1 depicts the scheme for the synthesis of the compounds of Formula XVI and Formula XVII.

The present invention provides a non-peptidic amino derivative having the general structure of Formula I,

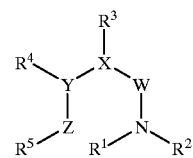

I wherein,
$R^1$, $R^3$, $R^4$ and $R^5$ are each independently hydrogen, $C_1$–$C_{10}$ alkyl, $C_1$–$C_{10}$ alkyl substituted with one or more substituents, $C_2$–$C_{10}$ alkenyl, $C_2$–$C_{10}$ alkenyl substituted with one or more substituents, $C_2$–$C_{10}$ alkynyl, $C_2$–$C_{10}$ alkynyl substituted with one or more substituents, $C_1$–$C_8$ alkoxy, $C_1$–$C_8$ alkoxy substituted with one or more substituents, $C_2$–$C_8$ alkoxycarbonyl, $C_2$–$C_8$ alkoxycarbonyl substituted with one or more substituents, $C_1$–$C_8$ thioalkyl, $C_1$–$C_8$ thioalkyl substituted with one or more substituents, $C_2$–$C_8$ acyl, $C_2$–$C_8$ acyl substituted with one or more substituents, $C_2$–$C_8$ acyloxy, $C_2$–$C_8$ acyloxy substituted with one or more substituents, aryloxy, aryl, aryl substituted with one or more substituents, $C_3$–$C_7$ cycloalkyl, $C_3$–$C_7$ cycloalkyl substituted with one or more substituents, $C_3$–$C_7$ heterocycle, or $C_3$–$C_7$ heterocycle substituted with one or more substituents, or any of these rings fused or spiro-fused to a cycloalkyl, heterocyclic or aromatic ring;

$R^2$ is hydrogen, straight or branched $C_1$–$C_6$ alkyl or $C_3$–$C_7$ cycloalkyl or $C_3$–$C_7$ cycloalkyl substituted with one or more substituents, $C_3$–$C_7$ heterocycle, $C_3$–$C_7$ heterocycle substituted with one or more substituents, aryl, aryl substituted with one or more substituents, heteroaryl, heteroaryl substituted with one or more substituents, or any of these rings fused or spiro-fused to a cycloalkyl, heterocyclic or aromatic ring; or $R^2$ together with $R^1$ forms a $C_2$–$C_7$ heterocycle, $C_2$–$C_7$ heterocycle substituted with one or more substituents, heteroaryl, or heteroaryl substituted with one or more substituents;

W is carbonyl (C=O), amido (NH(C=O)), amidoalkyl (NH(C=O)CH$_2$—), imino (C=NH), thiocarbonyl (C=S), sulfonyl (SO$_2$), methylene (CH$_2$), or methylene substituted with one or more substituents;

X is CH or N;

Y is CH or N; and

Z is carbonyl (C=O), amnino (NH), imino (C=N), sulfonyl (SO$_2$), or (C=O)NH; or Z, together with $R^1$, N, W, X, and Y, forms a $C_5$–$C_7$ heterocyclic ring in which $R^1$ is a direct bond or a $C_1$–$C_2$ alkylene.

With reference to Formula I, preferred FSH agonists are cyclic compounds wherein Z together with $R^1$, N, W, X, and Y form a $C_5$–$C_7$ heterocyclic ring in which $R^1$ is a direct bond or a $C_1$–$C_2$ alkylene and which is substituted with one or more substituents,

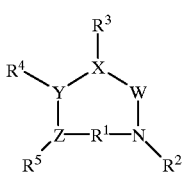

II

Also with reference to Formula I, additional preferred FSH agonists are cyclic compounds wherein $R^2$ and $R^3$ form a $C_5$–$C_7$ heterocycle substituted with one or more substituents:

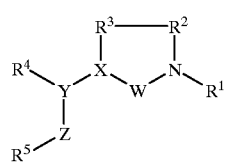

III

Additional preferred FSH agonists are compounds of Formula IV-A,

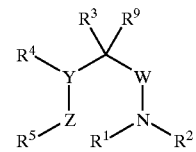

IV-A wherein $R^1$, $R^2$, $R^4$, $R^5$,

W, Y, and Z are as defined for Formula I; and $R^3$ and $R^9$ are each independently hydrogen, halogen, cyano, oxo, carboxy, formyl, nitro, amino, amidino, guanidino, $C_1$–$C_5$ alkyl or alkenyl or arylalkyl imino, azido, mercapto, carboxamido, hydroxy, hydroxyalkyl, alkylaryl, arylalkyl, $C_1$–$C_8$ alkyl, $C_1$–$C_8$ alkenyl, $C_1$–$C_8$ alkoxy, $C_1$–$C_8$ alkoxycarbonyl, $C_2$–$C_8$ acyl, $C_1$–$C_8$ alkylthio, arylalkylthio, arylthio, $C_1$–$C_8$ alkylsulfinyl, arylalkylsulfinyl, arylsulfinyl, $C_1$–$C_8$ alkylsulfonyl, arylalkylsulfonyl, arylsulfonyl, $C_1$–$C_6$ N-alkyl carbamoyl, $C_2$–$C_{15}$ N,N-dialkylcarbamoyl, $C_1$–$C_5$ alkyl or alkenyl or arylalkyl ester, $C_1$–$C_7$ cycloalkyl, aroyl, aryloxy, benzyloxy, benzyloxy substituted with one or more substituents, aryl, aryl substituted with one or more substituents, $C_3$–$C_7$ heterocycle, or any of these rings fused or spiro-fused to a cycloalkyl, heterocyclic or aromatic ring, —NR$^6$R$^7$ where R$^6$ and R$^7$ are as defined for Formula I, or —(CH$_2$)$_s$NR$^6$R$^7$ where s is 1–6 and R$^6$ and R$^7$ are as defined for Formula I. Additional preferred FSH agonists are compounds in which R$^3$ and R$^9$ of Formula IV-A together form a substituted or unsubstituted $C_3$–$C_7$ cycloalkyl or $C_3$–$C_7$ heterocycle spiro ring, or such a ring fused to a cycloalkyl, heterocyclic or aromatic ring:

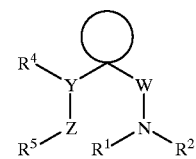

IV-B

Additional preferred FSH agonists are compounds of Formula V,

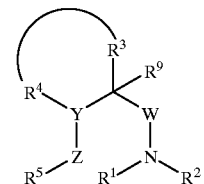

V wherein $R^3$ and $R^4$ together with the C and Y to which they are bound, respectively, form a substituted or unsubstituted aryl, substituted or unsubstituted $C_3$–$C_7$ cycloalkyl or $C_3$–$C_7$ heterocycle, or any of these rings fused or spiro-fused to a cycloalkyl, heterocyclic or aromatic ring, and $R^1$, $R^2$, $R^3$, $R^5$, $R^9$, W, Y, and Z are as defined for Formula I.

Also with reference to Formula I, additional preferred FSH agonists are cyclic α-aminocarboxamides wherein X=CH, Y=N, and $R^3$ and $R^4$ together with the carbon and nitrogen atoms to which they are attached form a heterocyclic or heteroaromatic ring,

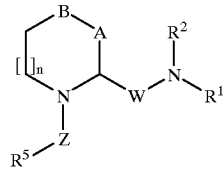

VI wherein $R^1$, $R^2$, $R^5$, W and Z are as defined for Formula I;
n=0 or 1; and
A and B are each independently —$CH_2$—, —$CH(R^{10})$—, —O—, —S—, —NH—, or —$NR^{10}$—, where $R^{10}$ is hydrogen, hydroxy, amino, amino substituted with one or more substituents, $C_1$–$C_6$ alkoxy, $C_1$–$C_6$ alkyl, $C_1$–$C_6$ alkyl substituted with one or more substituents, $C_1$–$C_6$ alkoxycarbonyl, cyano, $C_1$–$C_6$ aminoalkyl, or —$(CH_2)_s NR^6R^7$, where s, $R^6$, and $R^7$ are as defined for Formula I.

Additional preferred FSH agonists are compounds of Formula VII,

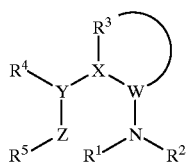

VII wherein $R^3$ and W form a substituted or unsubstituted aryl, substituted or unsubstituted $C_3$–$C_7$ cycloalkyl, $C_3$–$C_7$ heterocycle, or any of these rings fused or spiro-fused to a cycloalkyl, heterocyclic or aromatic ring, and $R^1$, $R^2$, $R^4$, $R^5$, X, Y, and Z are as defined for Formula I.

With reference to Formulae III and V, or V and VII, preferred FSH agonists are compounds wherein rings are combined to form fused bicyclic rings,

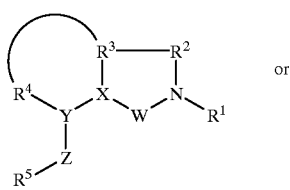

VIII-A or

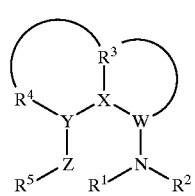

VIII-B wherein the rings in VIII-A and VIII-B are defined the same way as the corresponding rings in Formulae III, V, and VII.

With reference to Formulae I and V, additional preferred FSH agonists include compounds wherein Y=N and $R^3$ and $R^4$ together with the carbon and nitrogen atoms to which they are attached form a heterocyclic or heteroaromatic ring,

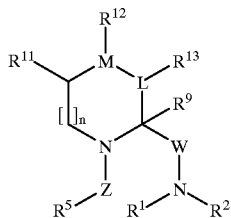

IX wherein $R^1$, $R^2$, $R^5$, $R^9$, W, and Z are as defined for Formula I;
$R^{11}$, $R^{12}$ and $R^{13}$ are defined the same way as $R^9$, and additionally, each of $R^9$, $R^{11}$, $R^{12}$, and $R^{13}$ either independently or in combination are capable of forming a spiro or fused or bridged ring;
n=or 1; and
L and M are independently CH, N, O, or S, provided L and M are not both heteroatoms and when L is O or S there is no $R^{13}$ and when M is O or S there is no $R^{12}$.

With reference to Formulae I and IV, preferred FSH agonists also include acyclic α-aminocarboxamides and spiro-ring containing α-aminocarboxamides of Formula X,

X-A

X-B wherein $R^1$, $R^2$, $R^3$, $R^4$, $R^5$, $R^9$, Z and the spiro ring are as defined for Formulae I and IV.

With reference to Formulae I and VII, preferred FSH agonists also include 2,3-diamino aryl or heteroaryl groups substituted with one or more substituents that are optionally fused to a cycloalkyl, heterocyclic, or aryl ring substituted with one or more substituents,

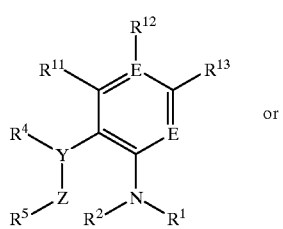

XI-A or

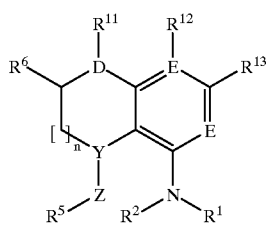

XI-B wherein E=Y=C or N;
$R^1$, $R^2$, $R^4$, $R^5$, $R^6$, $R^{11}$, $R^{12}$, $R^{13}$, B, Y and Z are as defined for Formulae I and IX; and
n=0 or 1.

Especially preferred FSH agonists are cyclic alpha-amino carboxamides that contain a heterocyclic or heteroaromatic ring,

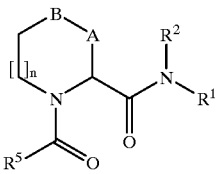

XII wherein $R^1$, $R^2$, $R^5$, n, A, and B are as defined for Formala VI.

Especially preferred FSH agonists based on Formula IX are cyclic alpha-amino carboxamides that contain a heterocyclic or heteroaromatic ring,

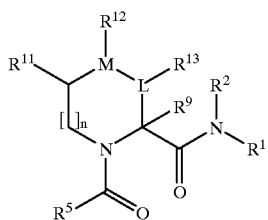

XIII wherein $R^1$, $R^2$, $R^5$, $R^9$, $R^{11}$, $R^{12}$, $R^{13}$, n, L, and M are as defined for Formula IX, and additionally, $R^{11}$ and $R^{12}$ together may form a fused substituted or unsubstituted aromatic ring.

Additional especially preferred FSH agonists based on Formula IX are cyclic compounds wherein W is amido rather than carbonyl (Formula XIII-A):

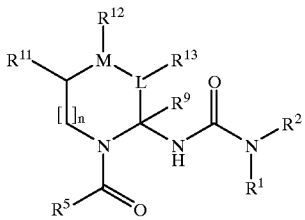

XIII-A

Especially preferred FSH agonists based on Formula XIII-A are compounds of Formula XIII-B,

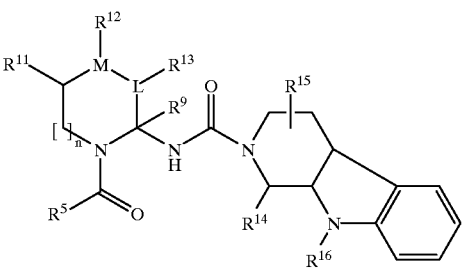

XIII-B wherein $R^{14}$ and $R^{15}$ are defined the same way as $R^9$ in Formula IV-A and $R^{16}$ is defined the same way as $R^2$ in Formula I.

Especially preferred FSH agonists related to compounds of Formula XIII-B are compounds of Formula XIII-C,

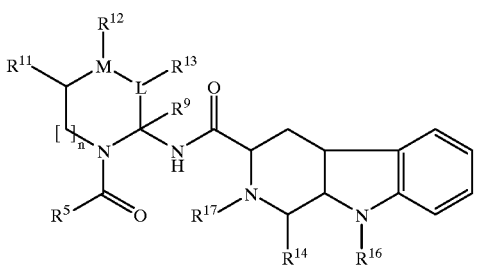

XIII-C wherein $R^{14}$ and $R^{16}$ are as defined for Formula XIII-B and $R^{17}$ is defined the same way as $R^2$ in Formula I.

Especially preferred FSH agonists based on Formula X are acyclic alpha-amino carboxamides or spiro-ring substituted alpha-amino-carboxamides, wherein either $R^3$ or $R^9$ is not hydrogen,

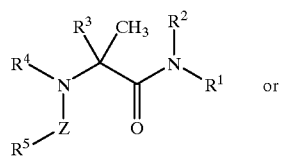

XIV-A or

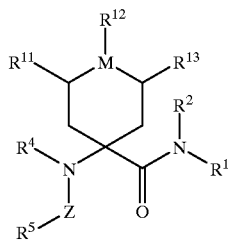

XIV-B wherein $R^1$, $R^2$, $R^4$, $R^5$, and Z are as defined for Formulae X-A and X-B, and $R^{11}$, $R^{12}$, $R^{13}$, and M are as defined for Formula IX.

Especially preferred FSH agonists based on Formula XI are 2-amino-3-carboxamido pyridines or the bicyclic analogs thereof,

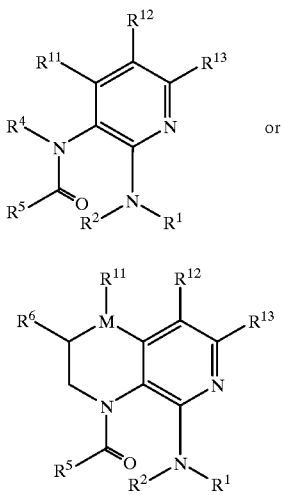

wherein $R^1$, $R^2$, $R^4$, $R^5$, $R^6$, $R^{11}$, $R^{12}$, $R^{13}$, and B are as defined for Formulae XI-A and XI-B.

Specific examples of compounds of Formula IX include the following:

1-[(2-Oxo-6-pentyl-2H-pyran)-3-carbonyl]-3-hydroxypyrrolidine-2-carboxylic acid-3-(9-ethylcarbazolyl)amide;

1-[(2-Oxo-6-pentyl-2H-pyran)-3-carbonyl]-3-acetoxypyrrolidine-2-carboxylic acid-3-(9-ethylcarbazolyl)amide;

1-[(2-Oxo-6-isopropyl-2H-pyran)-3-carbonyl]-piperidine-2-carboxylic acid-3-(9-ethylcarbazolyl) amide;

1-[(2-Oxo-6-n-propyl-2H-pyran)-3-carbonyl]-piperidine-2-carboxylic acid-3-(9-ethylcarbazolyl)amide;

1-[(2-Oxo-6-pentyl-2H-pyran)-3-carbonyl]-piperidine-2-carboxylic acid-2-(3-indolyl)ethylamide;

3-[(2-Oxo-6-pentyl-2H-pyran)-3-carbonyl]-2,2-dimethylthiazolidine-4-carboxylic acid-3-(9-ethylcarbazolyl)amide;

3-[(2-Oxo-6-pentyl-2H-pyran)-3-carbonyl]-5,5-dimethylthiazolidine-4-carboxylic acid-3-(9-ethylcarbazolyl)amide;

1-[(2-Oxo-6-pentyl-2H-pyran)-3-carbonyl]-4-methylpiperizine-2-carboxylic acid-3-(9-ethylcarbazolyl)amide;

2-[1-Carboxamido-2-(3H-imidazol-4-yl) ethylcarbamoyl]-N-(2-ethyl-n-hexylamino) tetrahydroisoquinoline;

1-[(2-Oxo-6-pentyl-2H-pyran)-3-carbonyl]-2-methylpyrrolidine-2-carboxylic acid-3-(9-ethylcarbazolyl) amide;

1-[(2-Oxo-6-pentyl-2H-pyran)-3-carbonyl]-4-hydroxypyrrolidine-2-carboxylic acid-3-(9-ethylcarbazolyl) amide;

1-[(2-Oxo-6-pentyl-2H-pyran)-3-carbonyl]-4-acetoxypyrrolidine-2-carboxylic acid-3-(9-ethylcarbazolyl) amide;

3-[(2-Oxo-6-pentyl-2H-pyran)-3-carbonyl]thiazolidine-4-carboxylic acid-3-(9-ethylcarbazolyl) amide;

3-[(2-Oxo-6-pentyl-2H-pyran)-3-carbonyl]-1,1-dioxothiazolidine-4-carboxylic acid-3-(9-ethylcarbazolyl) amide;

3-[(2-Oxo-6-pentyl-2H-pyran)-3-carbonyl]thiazolidine-2-carboxylic acid-3-(9-ethylcarbazolyl) amide;

1-(Benzofuran-2-yl)carbonyl-pyrrolidine-2-carboxylic acid-3-(9-ethyl carbazolyl)amide;

1-[(2-Oxo-6-methyl-2H-pyran)-3-carbonyl]-trans-3-azabicyclo(3.1.0)hexane-2-carboxylic acid-3-(9-ethylcarbazolyl)amide;

1-[(2-Oxo-6-pentyl-2H-pyran)-3-carbonyl]4-oxopyrrolidine-2-carboxylic acid-3-(9-ethylcarbazolyl)amide;

2-[(2-Oxo-6-pentyl-2H-pyran)-3-carbonyl]7-hydroxytetrahydroisoquinoline-3-carboxylic acid-3-(9-ethylcarbazolyl)amide;

2-[(2-Oxo-6-pentyl-2H-pyran)-3-carbonyl] tetrahydroisoquinoline-3-carboxylicacid-3-(9-ethylcarbazolyl)amide;

1-[(2-Oxo-6-pentyl-2H-pyran)-3-carbonyl]azetidine-2-carboxylic acid-3-(9-ethylcarbazolyl)amide;

1-[(2-Oxo-6-pentyl-2H-pyran)-3-carbonyl]3,4-dehydropyrrolidine-2-carboxylic-acid-3-(9-ethylcarbazolyl)amide;

1-(2-Oxo-2H-chromene-3-carbonyl)-pyrrolidine-2-carboxylic acid-3-(9-ethylcarbazolyl)amide;

1-(1,3-Dioxo-2-isoindolineacetyl)-piperidine-2-carboxylic acid-3-(9-ethylcarbazolyl)amide;

1-(2-Fluoro-4-trifluoromethylbenzoyl)-piperidine-2-carboxylic acid-3-(9-ethylcarbazolyl)amide;

1-(4-n-Pentylbenzoyl)-pyrrolidine-2-carboxylic acid-3-(9-ethylcarbazolyl)amide;

1-(4-n-butoxybenzoyl)-pyrrolidine-2-carboxylic acid-3-(9-ethylcarbazolyl)amide;

1-(4-n-Pentylbenzoylmethyl)-piperidine-2-carboxylic acid-3-(9-ethylcarbazolyl)amide;

1-[(2-Oxo-6-pentyl-2H-pyran)-3-carbonyl]-2-oxo-imidazolidine-5-carboxylic acid-3-(9-ethylcarbazolyl) amide;

1-[(2-Oxo-6-pentyl-2H-pyran)-3-carbonyl]-2-[(9-ethylcarbazolyl)aminomethyl] pyrrolidine;

1-[(2-Oxo-6-phenyl-2H-pyran)-3-carbonyl]-pyrrolidine-2-carboxylic acid-3-(9-ethylcarbazolyl)amide;

1-[(2-Oxo-6-methyl-2H-pyran)-3-carbonyl]-pyrrolidine-2-carboxylic acid-3-(9-ethylcarbazolyl)amide;

1-[(2-Oxo-6-phenyl-2H-pyran)-3-carbonyl]-piperidine-2-carboxylic acid-3-(9-ethylcarbazolyl)amide; and 1-[(2-Oxo-6-methyl-2H-pyran)-3-carbonyl]-piperidine-2-carboxylic acid-3-(9-ethylcarbazolyl)amide;

or a pharmaceutically acceptable addition salt thereof.

Specific examples of compounds of Formula XII include the following:

2-[ 1-Carboxamido-2-(3H-imidazol-4-yl) ethylcarbamoyl]-2-(2-ethyl-n-hexylamino)tetraline;

2-(2-Ethyl-n-hexyl)-N-[(1-carboxamido-2-terazolyl) ethyl]-3-isoquinolinecarboxamide;

1-[(2-Oxo-6-pentyl-2H-pyran)-3-carbonyl]pyrrolidine-2-carboxylic acid-3-(9-ethylcarbazolyl)amide; and 1-[(2-Oxo-6-pentyl-2H-pyran)-3-carbonyl]piperidine-2-carboxylic acid-3-(9-ethylcarbazolyl)amide;
or a pharmaceutically acceptable addition salt thereof.

Specific examples of compounds represented by Formula XIII include the following:

1-[(2-Oxo-6-pentyl-2H-pyran)-3-carbonyl]pyrrolidine-2-carboxylic acid-3-(9-ethylcarbazolyl) amide (Formula XVI),

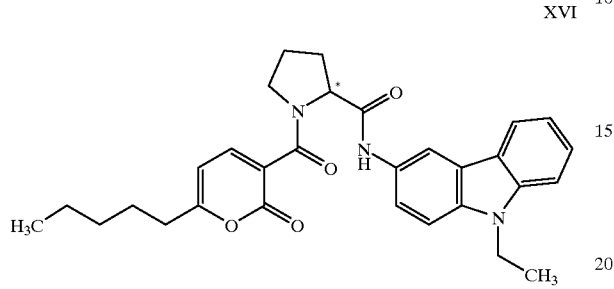

XVI which can exist in two enantiomeric forms (the asterisk denotes the chiral center);

1-[(2-Oxo-6-pentyl-2H-pyran)-3-carbonyl]piperidine-2-carboxylic acid-3-(9-ethyl carbazolyl)amide (Formula XVII),

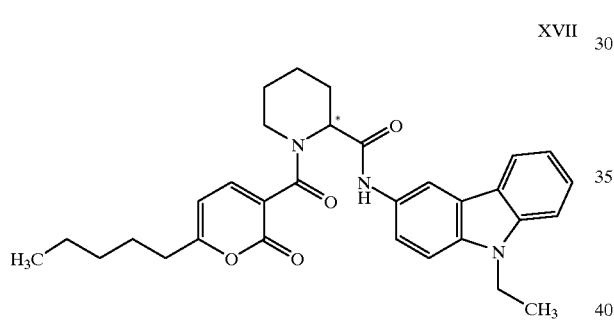

XVII which can exist in two enantiomeric forms (the asterisk denotes the chiral center);

2-(2-Ethyl-n-hexyl)-N-[(1 -carboxamido-2-terazolyl) ethyl]-3-isoquinolinecarboxamide (Formula XVIII),

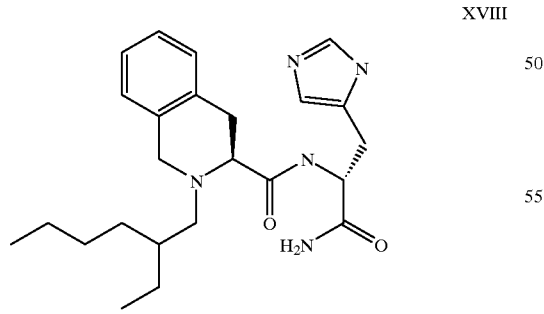

XVIII

1-[(2-Oxo-6-pentyl-2H-pyran)-3-carbonyl]-4-hydroxypyrrolidine-2-carboxylic acid-3-(9-ethylcarbazolyl) amide (Formula XIX),

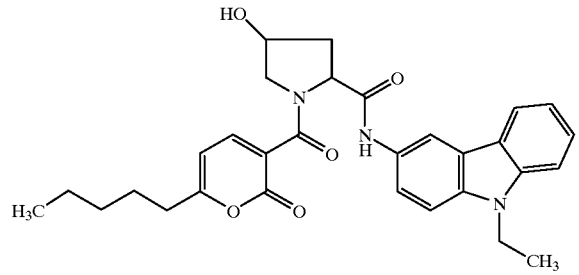

XIX

1-[(2-Oxo-6-pentyl-2H-pyran)-3-carbonyl]-2-methylpyrrolidine-2-carboxylicacid-3-(9-ethylcarbazolyl) amide (Formula XX),

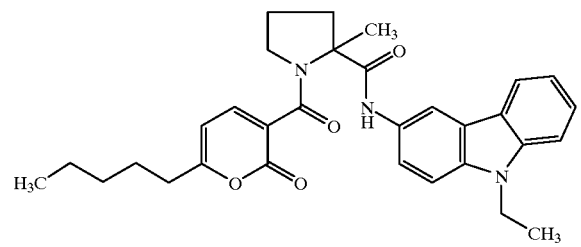

XX

1-[(2-Oxo-6-pentyl-2H-pyran)-3-carbonyl]-2-[3-(9-ethylcarbazolyl)aminomethyl] pyrrolidine Formula XXI),

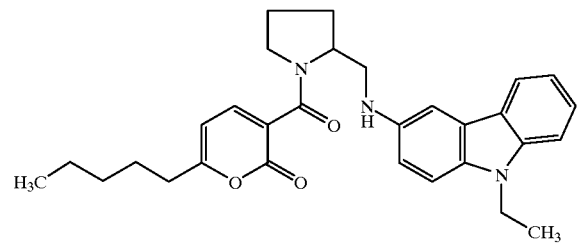

XXI

2-[1-Carboxamido-2-(3H-imidazol-4-yl) ethylcarbamoyl]-N-(2-ethyl-n-hexylamino)-tetrahydroisoquinoline (Formula XXII),

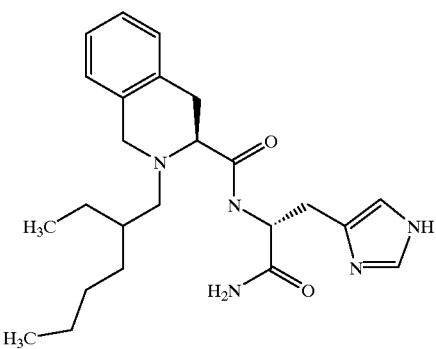

or a pharmaceutically acceptable addition salt thereof.

Specific examples of compounds represented by Formula XIV include the following:

1-[3-(9-Ethylcarbazolyl)carbamoyl]ethylamino-N-methyl-(2-oxo-6-pentyl-2H-pyran-3-carboxamide) (Formula XXIII) and 1-Methyl-i-[3-(9-ethylcarbazolyl)carbamoyl]-ethylamino-N-methyl-(2-oxo-6-pentyl-2H-pyran-3-carboxamide) (Formula XXIV),

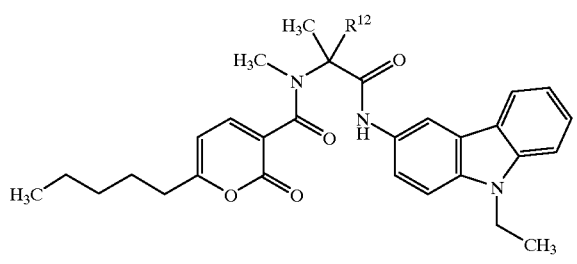

XXIII ($R^{12}$ = H); XXIV ($R^{12}$ = $CH_3$)

2-[(1-Carboxamido-2-terazolyl)ethylcarbamoyl]-(D,L)-2-(2-ethyl-n-hexylamino)tetraline (Formula XXV),

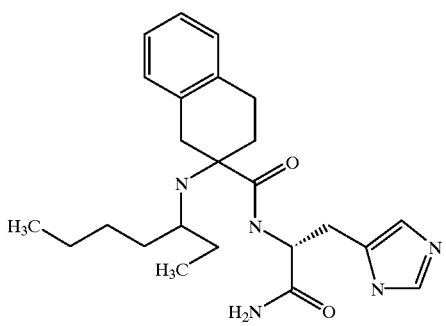

2-[(1-Carboxamido-2-terazolyl)ethylcarbamoyl]-2-(2-ethyl-n-hexylamino)tetraline;
1-[3-(9-Ethylcarbazolyl)carbamoyl]ethylamino-N-methyl-(2-oxo-6-pentyl-2H-pyran-3-carboxamide);
1-Methyl-1-[3-(9-ethylcarbazolyl)carbamoyl]-ethylamino-N-methyl-(2-oxo-6-pentyl- H-pyran-3-carboxamide);
1-[3-(9-Ethylcarbazolyl)carbamoyl]isoamylamino-N-methyl-(2-oxo-6-pentyl-2H-pyran-3-carboxamide);
1-[3-(9-Ethylcarbazolyl)carbamoyl]isobutylamino-N-methyl-(2-oxo-6-pentyl-2H-pyran-3-carboxamide);
1-[3-(9-Ethylcarbazolyl)carbamoyl]phenylethylamino-N-methyl-(2-oxo-6-pentyl-2H-pyran-3-carboxamide);
1-[3-(9-Ethylcarbazolyl)carbamoyl]2-hydroxyethylamino-N-methyl-(2-oxo-6-pentyl-2H-pyran-3-carboxamide);
1-[3-(9-Ethylcarbazolyl)carbamoyl]methylamino-N-methyl-(2-oxo-6-pentyl-2H-pyran-3-carboxamide);
1-[3-(9-Ethylcarbazolyl)carbamoyl]methylamino-N-ethyl-(2-oxo-6-pentyl-2H-pyran-3-carboxamide); and
1-Methyl-1-[3-(9-ethylcarbazolyl)carbamoyl]-ethylamino-(2-oxo-6-pentyl-2H-pyran-3-carboxamide);

or a pharmaceutically acceptable addition salt thereof.

Specific examples of compounds represented by Formula XV include the following:

3-(9-ethylcarbazolyl)amino-pyridin-2-yl-3-(2-oxo-6-pentyl-2H-pyran-3-carboxamide) (Formula XXVI) and 3-(9-ethylcarbazolyl)amino-pyridin-2-yl-3-(N-methyl-2-oxo-6-pentyl-2H-pyran-3-carboxamide) (Formula XXVII),

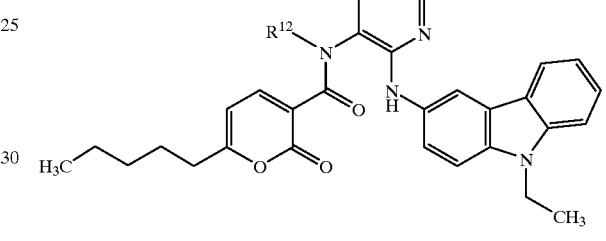

XXVI ($R^{12}$ = H); XXVII ($R^{12}$ = $CH_3$)

or a pharmaceutically acceptable addition salt thereof.

It will be appreciated by those skilled in the art that compounds of the invention may contain a chiral center, and thus will exist in two enantiomeric forms. The present invention includes the use of the individual enantiomers and mixtures of the enantiomers. The enantiomers may be resolved by methods known to those skilled in the art, for example by formation of diastereomeric complexes or derivatives which may be separated, for example, by crystallization or chromatographic separation. Alternatively, specific enantiomers may be synthesized by asymmetric synthesis using optically active reagents, substrates, catalysts or solvents, or by converting one enantiomer to the other by asymmetric transformation.

The non-peptidic amino derivatives of the present invention represent small molecule substitutes for FSH for the treatment of infertility. The invention therefore comprises a pharmaceutical composition comprising a compound of any of Formulas I-XXVII and a pharmaceutically acceptable carrier, diluent, or excipient thereof.

The invention further comprises a pharmaceutical composition comprising a compound of any of Formulas I-XXVII and a pharmaceutically acceptable carrier, diluent, or excipient thereof in combination with FSH.

The invention further comprises a pharmaceutical composition comprising a compound of any of Formulas I-XXVII and a pharmaceutically acceptable carrier, diluent, or excipient thereof in combination with the anti-estrogen compound Clomiphene citrate (Cassidenti et al. (1992) *Hum. Reprod.*, 7: 344–348).

The invention further comprises a pharmaceutical composition comprising a compound of any of Formulas I–XXVII and a pharmaceutically acceptable carrier, diluent, or excipient thereof in combination with human chorionic gonadotropin (hCG) or human pituitary leutenizing hormone (LH) (Breckwoldt et al. (1971) Fert. Steril., 22: 451–455; Diedrich et al. (1988) Hum. Reprod., 3: 39–44).

The invention further comprises use of a compound of Formulas I to XXIX for the preparation of a medicament.

The invention further comprises a method for treating infertility comprising administering an effective FSH agonistic amount of any of said pharmaceutical compositions.

As FSH agonists, the compounds of the invention are also useful research tools to study the role of FSH and the FSH receptor in biological processes in vitro.

Chemical Syntheses

The invention provides such processes for the preparation of the compounds of Formula I, which are described hereinafter, which processes comprise reacting a compound of Formula XXVIII,

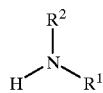

XXVIII with a compound of Formula XXIX,

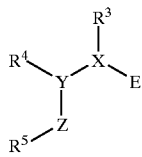

XXIX wherein $R^1$, $R^2$, $R^3$, $R^4$, $R^5$, X, Y, and Z are defined as for Formula I and E represents a functional group such as $SO_2Cl$, CHO, COOH, COCl, NCO, CN, N=C—Cl, $CH_2Cl$, or $CH_2O$-tosylate.

The compounds of the invention may be prepared by the methods described below and in Examples 1–5. The synthetic schemes displayed in FIGS. 1–5 illustrate how compounds according to the invention can be made. Those skilled in the art will be able to routinely modify and/or adapt the methods and schemes presented herein to synthesize any compound of the invention.

Pharmaceutical Preparations

Pharmaceutical compositions comprising a compound of Formulas I to XXIX and a pharmaceutically acceptable carrier, diluent or excipient therefore are also within the scope of the present invention. Thus, the present invention also provides compounds for use as a medicament. In particular, the invention provides the compounds of Formulas I to XXIX for use as FSH agonists, for the treatment of infertility, either alone or in combination with other medicaments. In in vitro assays these compounds were found to mimic the actions of FSH since they exhibit positive log dose response in the screening assay (CHO luciferase FSHR) and are negative in the control assay (CHO luciferase). Accordingly, the compounds of the invention are useful research tools for studying the role of FSH in biological processes.

The representative compounds also show activity in the primary rat granulosa cell bioassay, which is used to detect the conversion of testosterone to estradiol in the presence of FSH or an FSH agonist. The CHO luciferase assay and the rat granulosa cell bioassay are described in detail hereinafter.

The compounds of the invention, together with a conventional adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed. Tablets containing 10 milligrams of active ingredient or, more broadly, 0.1 to 100 milligrams, per tablet, are accordingly suitable representative unit dosage forms.

Definitions

The following paragraphs provide definitions of the various chemical moieties that make up the compounds of the invention and are intended to apply uniformly throughout the specification and claims unless expressly stated otherwise.

The term "substituent" refers to (a) halogen, cyano, oxo, carboxy, formyl, nitro, amino, amidino, guanidino, $C_1$–$C_5$ alkyl or alkenyl or arylalkyl imino, carbamoyl, azido, carboxamido, mercapto, hydroxy, hydroxyalkyl, alkylaryl, arylalkyl, $C_1$–$C_8$ alkyl, $C_1$–$C_8$ alkenyl, $C_1$–$C_8$ alkoxy, $C_1$–$C_8$ alkoxycarbonyl, aryloxycarbonyl, $C_2$–$C_8$ acyl, $C_1$–$C_8$ alkylthio, arylalkylthio, arylthio, $C_1$–$C_8$ alkylsulfinyl, arylalkylsulfinyl, arylsulfinyl, $C_1$–$C_8$ alkylsulfonyl, arylalkylsulfonyl, arylsulfonyl, $C_1$–$C_6$ N-alkyl carbamoyl, $C_2$–$C_{15}$ N,N-dialkylcarbamoyl, $C_3$–$C_7$ cycloalkyl, aroyl, aryloxy, arylalkyl ether, aryl, aryl fused to a cycloalkyl or heterocycle or another aryl ring, $C_3$–$C_7$ heterocycle, or any of these rings fused or spiro-fused to a cycloalkyl, heterocyclic, or aromatic ring; or (b) $NR^6R^7$, where $R^6$ and $R^7$ are each independently hydrogen, cyano, oxo, carboxamido, amidino, $C_1$–$C_8$ hydroxyalkyl, $C_1$–$C_3$ alkylaryl, aryl-$C_1$–$C_3$ alkyl, $C_1$–$C_8$ alkyl, $C_1$–$C_8$ alkenyl, $C_1$–$C_8$ alkoxy, $C_1$–$C_8$ alkoxycarbonyl, aryloxycarbonyl, aryl-$C_1$–$C_3$ alkoxycarbonyl, $C_2$–$C_8$ acyl, $C_1$–$C_8$ alkylsulfonyl, arylalkylsulfonyl, arylsulfonyl, aroyl, aryl, aryl fused to a cycloalkyl or heterocyclic or another aryl ring, $C_3$–$C_7$ cycloalkyl, $C_3$–$C_7$ heterocycle, or any of these rings fused or spiro-fused to a cycloalkyl or heterocyclic or aromatic ring;

or where $R^6$ and $R^7$ are taken together to form —$(CH_2)_m$B$(CH_2)_n$— where B is —C(H)($R^8$)—, —O—, —N($R^8$)—, or —S(O)$_r$—, where m and n are independently 1 to 3, r is 0 to 2, and $R^8$ is defined the same way as $R^6$; or (c) —$(CH_2)_s$$NR^6R^7$ where s is 1–6 and $R^6$ and $R^7$ are defined as in section (b) of the definition of substituent, above.

The term "substituted" refers to the moiety substituted with one or more substituents.

The term "alkyl" refers to a univalent $C_1$ to $C_8$ saturated straight, branched, or cyclic alkane moiety and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The alkyl group can be optionally substituted with any appropriate group, including but not limited to one or more moieties selected from the group consisting of halo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art or as taught, for example, in Greene, et al., "Protective Groups in Organic Synthesis," John Wiley and Sons, Second Edition, 1991.

The term "cycloalkyl" refers to a monocyclic $C_3$–$C_7$ ring.

The terms "arylalkyl" and "alkylaryl" refer to groups in which the alkyl consists of between 1 and 3 carbons.

The term "alkoxy" refers to an alkyl moiety having a terminal —O— with free a valence, e.g., $CH_3CH_2$—O—

The term "alkenyl" refers to a univalent $C_2$–$C_6$ straight, branched, or in the case of $C_{5-6}$, cyclic hydrocarbon with at least one double bond, optionally substituted as described above.

The term "alkynyl" refers to a univalent $C_2$ to $C_6$ straight or branched hydrocarbon with at least one triple bond (optionally substituted as described above) and specifically includes acetylenyl, propynyl, and —C≡—C—$CH_2$(alkyl), including —C≡—C—$CH_2$($CH_3$).

The term "aryl" refers to a mono- or bi- or tri-cyclic aromatic ring system that may optionally be substituted with one or more substituents.

The term "heteroatom" means N, O, or S.

The term "heterocycle" refers to a cyclic alkyl, alkenyl, or alkynyl moiety wherein one or more ring carbon atoms is replaced with a heteroatom; a Cm—Cn heterocycle is a ring that contains m to n members wherein one or more of the members is a heteroatom.

The term "heteroaryl" refers to a aryl moiety wherein one or more ring carbon atoms is replaced with a heteroatom.

The term "halo" refers to chloro, fluoro, iodo, or bromo.

When a substituent defined as a monovalent radical becomes incorporated into a ring (e.g., $R^2$ and $R^3$ on Formula III), it is understood that the substituents become the corresponding divalent radicals.

The term "pharmaceutically acceptable salts or complexes" refers to salts or complexes that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, methanesulfonic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The term "pharmaceutically active derivative" refers to any compound that upon administration to the recipient, is capable of providing directly or indirectly, the compounds disclosed herein.

EXAMPLES

The following Examples further illustrate specific aspects of the present invention. It is to be understood, however, that these examples are included for illustrative purposes only and are not intended to limit the scope of the invention in any respect and should not be so construed.

Example 1

Synthesis of 1-[(2-Oxo-6-Pentyl-2H-Pyran)-3-Carbonyl]-Pyrrolidine-2-Carboxylic Acid-3-(9-Ethyl Carbazolyl) Amide (Formula XVI) (FIG. 1; Scheme 1)

Step A. Synthesis of 1-[(2-Oxo-6-Pentyl-2H-Pyran)-3-Carbonyl]-Pyrrolidine-2-Carboxylic Acid-t-Butylester:

To a solution of Boc-L-Proline (5 mmol, Advanced ChemTech, Louisville, USA) in dichloromethane (20 mL) cooled to 0° C. were added dropwise a solution of di-isopropyl carbodiimide (DIC, 2.5 mmol). After the solution had been stirred at 0° C. for 30 min, the solid by-product (DIC urea) was filtered out. To the filtrate were added 3-amino-9-ethylcarbazole (5 mmol, Aldrich Chemical Company, Milwaukee, USA) in DMF and triethyl amine (5 mmol) and the solution was stirred at room temperature for 16 h. The reaction was monitored by TLC for completion. The solution was evaporated to dryness under vacuum. The residue was dissolved in ethyl acetate (250 mL) and washed successively with 10% aqueous sodium carbonate, 10% aqueous citric acid, water, and saturated brine. The organic layer was dried on anhydrous sodium sulfate, filtered and ethyl acetate was evaporated to give an oily product 1-(t-Butoxycarbonyl)-N-[3-(9-ethylcarbazolyl)]-2-pyrrolidinecarboxamide (75% yield); HPLC purity: 90%; Mass: desired M+H found (Perceptive Biosystem's Voyager-Maldi TOF). This compound was used in the next step without further purification.

Step B. Formation of 1-[(2-Oxo-6-Pentyl-2H-Pyran)-3-Carbonyl]-Pyrrolidine-2-Carboxylic Acid-3-(9-Ethyl Carbazolyl)Amide (Formula XVI):

The N-Boc-pyrrolidine carboxamide obtained from step A was dissolved in 50% trifluoroacetic acid/dichloromethane (25 mL) and stirred for 30 min at room temperature. The TFA solution was evaporated under vacuum. The dry residue was dissolved in DMF and two equivalents of triethyl amine was added, followed by one equivalent of a symmetrical anhydride (generated in situ from 2-oxo-6-pentyl-2H-pyran-3-carboxylic acid and diisopropylcarbodi-imide) and the solution was stirred for 14 h. DMF was evaporated under high vacuum. The residue was dissolved in ethyl acetate. This organic layer was washed with 10% aqueous sodium carbonate, 10% aqueous citric acid, water and saturated brine. The organic layer was dried on anhydrous magnesium sulphate. The organic layer was decolorized with charcoal evaporated under vacuum to result in light brown gummy material. This crude material was purified on preparative reverse phase HPLC using 1% TFA-acetonitrile and water as the mobile phase. HPLC purity>95%.%; Mass: calculated for $C_{30}H_{33}N_3O_4$: 499.6; found: 500.6 (M+H) (Perceptive Biosystem's Voyager-Maldi TOF).

Synthesis of 1-[(2-Oxo-6-pentyl-2H-pyran)-3-carbonyl]-piperidine-2-carboxylic acid-3-(9-ethyl carbazolyl)amide (Formula XVII) was achieved using the same procedure as above by using N-boc-pipecolinic acid made from dl-pipecolinic acid (Aldrich Chemical Company, Milwaukee, USA) in place of Boc-L-proline.

Figure 2:
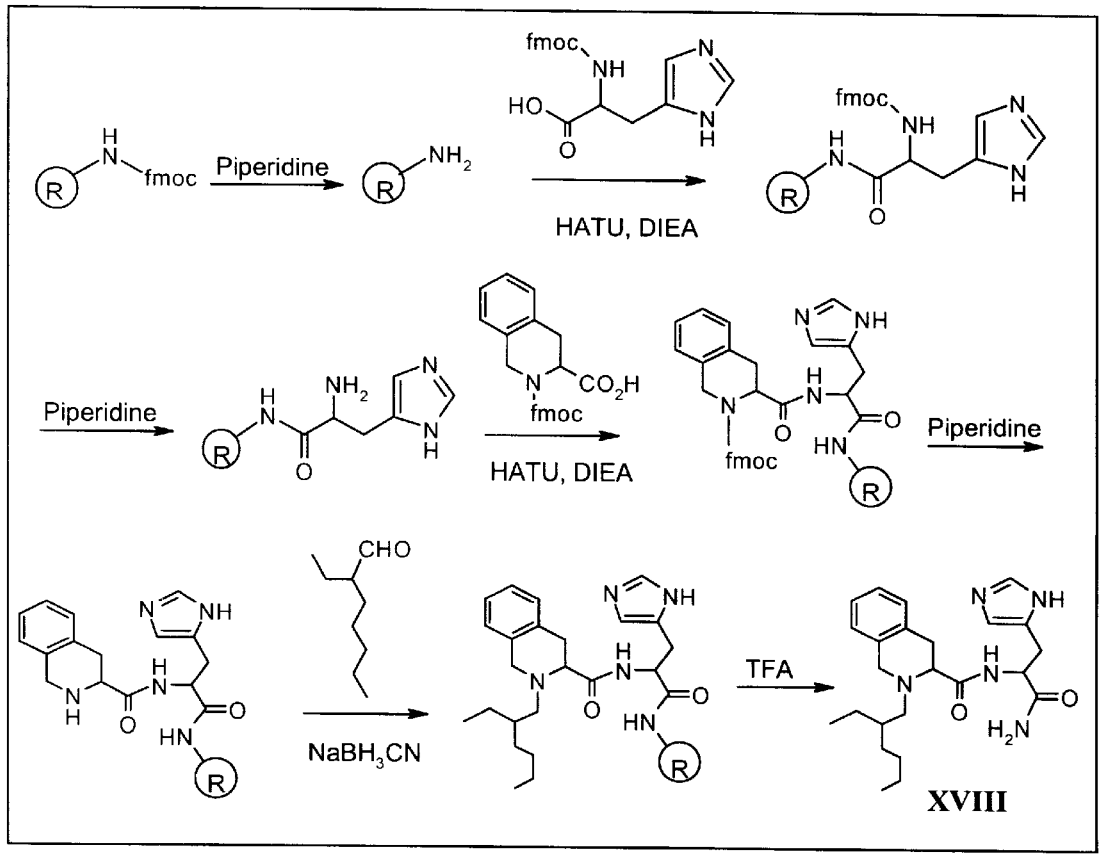
FIG. 2 depicts the scheme for the synthesis of the compound of Formula XVIII.

Example 2
Synthesis of 2-(2-Ethyl-n-Hexyl)-N-[(1-Carboxamido-2-Terazolyl)Ethy]-3-Isoquinolinecarboxamide (Formula XVIII) (FIG. 2; Scheme 2)

Step A. Synthesis of Amide of Rink Amide Resin and N-Fmoc-D-Histidine:

Fmoc-amino Rink Amide resin (1.0 g, 0.45 mmol/g substitution), available from NovaBiochem (San Diego, USA), was swollen with dichloromethane for 10 min. The resin was further washed with dimethyl formamide three times. The Fmoc- group was removed with 20% piperidine in DMF for 30 min. Further repeated washings were done with DMF (3×2 min), dichloromethane (DCM, 3×2 min), DMF (1×1 min). Then N-Fmoc-D-histidine (available from Advanced ChemTech, Louisville, USA) in DMF [10 mL, 2.0 mmol (4 equivalents with respect to the resin loading)], 2 mmol of O-(7-azabenzotriazol-1-yl)-1,1,3,3-tetramethyluronium hexafluorophosphate (HATU) and 4 mmol of diisopropylethylamine (DIEA, 640 µL) were added to the resin to make a slurry. This slurry was stirred at room temperature for 2 h. The small resin sample was subjected to Sarin-Kaiser test for the completion of reaction. The resin was then filtered and washed with DMF (3×2 min), MeOH (2×2 min), dichloromethane (2×2 min) and DMF (2×2 min).

Step B. Synthesis of N-[(1-Carboxamido-2-Tetrazoyl)Ethyl]-3-Isoquinoline-Carboxamide Bound to Rink Amide Resin:

The compound obtained from step A was deprotected by removal of the Fmoc- group with 20% piperidine in DMF for 30 min. Further resin washings were done with DMF (3×2 min), dichloromethane (DCM, 3×2min), DMF (1×1 min). Then (S)-(-)-1,2,3,4-tetrahydro-3-isoquinolinecarboxylic acid (available from Advanced ChemTech, Louisville, USA) in DMF [10 mL, 2.0 mmol (4 equivalents with respect to the resin loading)], 2 mmol of HATU and 4 mmol of diisopropylethylamine (DIEA, 640 µL) were added to the resin to make a slurry. This slurry was stirred at room temperature for 2 h. The small resin sample was subjected to Sarin-Kaiser test for the completion of reaction. The resin was then filtered and washed with DMF (3×2 min), MeOH (2×2 min), dichloromethane (2×2 min) and DMF (2×2 min).

Step C. Synthesis of 2-(2-Ethyl-n-Hexyl)-N-[(1-Carboxamido-2-Terazolyl)Ethyl]-3-Isoquinolinecarboxamide Bound to Resin:

The Fmoc- group on the tetrahydroisoquinoline nitrogen was removed by treatment with 20% piperidine in DMF for 30 min. The resin was then washed with DMF (3×2 min), dichloromethane (3×2 min), and DMF (1×1 min). Then a 0.2 M stock solution of 2-ethylhexanal (Aldrich Chemical Company, Milwaukee, USA) in 2% Acetic acid in trimethyl ortho formate (TMOF) (10 mL/g of resin) was added and reaction was carried out for 2 h to form an imine derivative in situ. Then a 0.2 M stock solution of sodium cyanoborohydride (NaCNBH$_3$) in TMOF was added to the above reaction mixture to get the final concentration to 0.1 M and the reaction was continued at room temperature for 14 h. The resin was washed with TMOF (3×2 min), DMF (3×2 min), MeOH (3×2 min), dichloromethane (2×2 min) and dried under vacuum for 4 h.

Step D. Formation of 2-(2-Ethyl-n-Hexyl)-N-[(1-Carboxamido-2-Terazolyl)Ethyl]-3-Isoquinoline Carboxamide (Formula XVIII):

Pre-cooled cleavage reagent (trifluoroacetic acid:dimethylsulfide:triisopropylsilane:H$_2$O; 90:2.5:2.5:5; v/v) was added (10 mL/g) to the dried resin and allowed to stir for 2 h at room temperature. The TFA cocktail was filtered into a 20 mL vial and TFA was evaporated on a rotavapor under vacuum. Diethyl ether was added to precipitate the compound along with trityl alcohol. The mixture was dissolved in 20% acetonitrile before purification on reverse phase HPLC.

Step E. Purification of Compound XVIII:

The crude compound from step D was dissolved in 10% aqueous acetonitrile and loaded onto the C18 column on Delta preparative HPLC. A linear gradient with 1% TFA acetonitrile and water was used as mobile phase. HPLC purity>95%; Mass (Perceptive Biosystem's Voyager-Maldi TOF): calculated for $C_{24}H_{35}N_5O_2$: 425.6; found: 426.6 (M+H).

Figure 3:
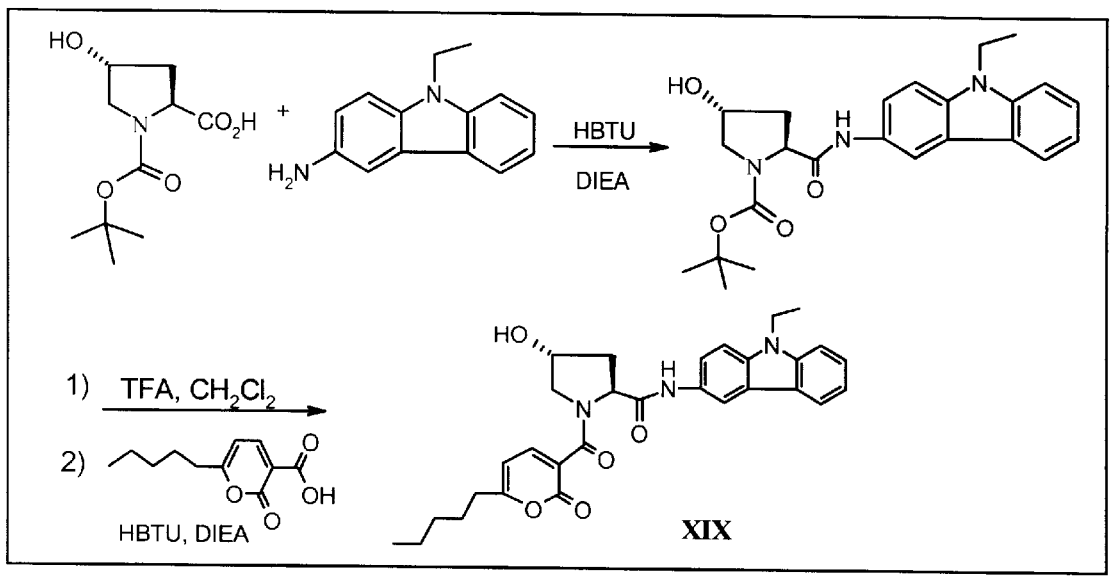
FIG. 3 depicts the scheme for the synthesis of the compound of Formula XIX.

Example 3
Synthesis of 1-[(2-Oxo-6-Pentyl-2H-Pyran)-3-Carbonyl]-4-Hydroxypyrrolidine-2-Carboxylic Acid-[3-(9-Ethyl Carbazolyl)] Amide (Formula XIX) (FIG. 3; Scheme 3)

Step A. Synthesis of 1-t-Butoxycarbonyl-4-Hydroxypyrrolidine-2-Carboxylic Acid-[3-(9-Ethyl Carbazolyl)] Amide:

To a solution of N-Boc-trans-hydroxy-L-proline (5 mmol, Sigma Chemical Company, St. Louis, USA) in dichloromethane (20 mL) at ambient temperature were added at 5 min intervals 2-(1H-benzotriazol-1-yl)-1,1,3,3-tetramethyluronium hexafluorophosphate (HBTU, 5 mmol), diisopropyl ethyl amine (DIEA, 10 mmol) followed by 3-amino-9-ethylcarbazole (5 mmol, Aldrich Chemical Company, Milwaukee, USA). After stirring for 1 h, the solution was evaporated to dryness under vacuum. The residue was dissolved in ethyl acetate (250 mL) and washed successively with 10% aqueous sodium carbonate, 10% aqueous citric acid, water, and saturated brine. The organic layer was dried on anhydrous sodium sulfate, filtered and ethyl acetate was evaporated to give an oily product 1-(t-butoxycarbonyl)-4-hydroxypyrrolidine- 2-[3-(9-ethyl carbazolyl)] carboxamide (85% yield); HPLC purity: 90%. This compound was used in the next step without further purification.

Step B. Formation of 1-[3-(2-Oxo-6-Pentylpyran) Carbonyl]-4-Hydroxypyrrolidine-2-Carboxylic Acid-3-(9-Ethyl Carbazolyl)Amide:

The 1-(t-butoxycarbonyl)-4-hydroxypyrrolidine-2-[3-(9-ethyl carbazolyl)] carboxamide obtained from step A was dissolved in 50% trifluoro acetic acid/dichloromethane (25 mL) and stirred for 30 min at room temperature. The TFA solution was evaporated under vacuum. The dry residue was dissolved in dichloromethane and added to the activated ester of 2-oxo-6-pentyl-2H-pyran-3-carboxylic acid (generated in situ from 5 mmol 2-oxo-6-pentyl-2H-pyran-3-carboxylic acid, 5 mmol HBTU and 10 mmol diisopropylethylamine) and the solution was stirred for 1 h. The solvent was evaporated under vacuum and the residue was dissolved in ethyl acetate. This organic layer was washed with 10% aqueous sodium carbonate, 10% aqueous citric acid, water and saturated brine. The organic layer was dried on anhydrous magnesium sulphate and then evaporated in vacuo to result in light brown gummy material. This crude material was purified on preparative reverse phase HPLC using 1% TFA-acetonitrile and water as the mobile phase. HPLC purity >95%. %; Mass: calculated for $C_{30}H_{33}N_3O_5$: 415.6; found: 516 (Perceptive Biosystem's Voyager-Maldi TOF).

Figure 4:
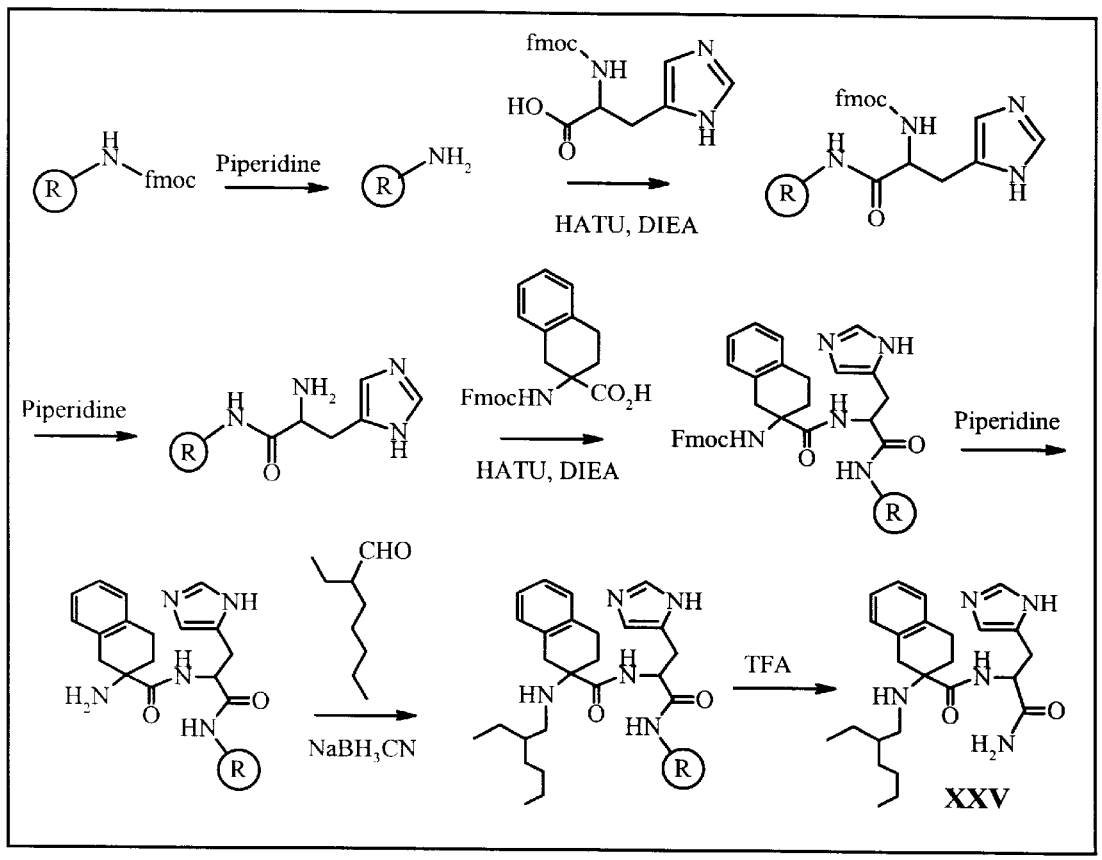
FIG. 4 depicts the scheme for the synthesis of the compound of Formula XXV.

Example 4
Synthesis of 2-[(1-Carboxamido-2-Terazolyl) Ethylcarbamoyl]-(D,L)-2-(2-ethyl-n-hexylamino)tetraline (Formula XXV) (FIG. 4; Scheme 4)

Step A. Synthesis of Amide of Rink Amide Resin and N-Fmoc-D-Histidine:

Fmoc-amino Rink Amide resin (1.0 g, 0.45 mmol/g substitution), available from NovaBiochem (San Diego, USA), was swollen with dichloromethane for 10 min. The resin was further washed with dimethyl formamide three times. The Fmoc group was removed with 20% piperidine in DMF for 30 min. Further repeated washings were done with DMF (3 ×2 min), dichloromethane (DCM, 3×2 min), DMF (1×1 min). Then N-Fmoc-D-histidine (available from Advanced ChemTech, Louisville, USA) in DMF [10 mL, 2.0 mmol (4 equivalents with respect to the resin loading)], 2 mmol of O-(7-azabenzotriazol-1-yl)-1,1,3,3-tetramethyluronium hexafluorophosphate (HATU) and 4 mmol of diisopropylethylamine (DIEA, 640 uL) were added to the resin to make a slurry. This slurry was stirred at room temperature for 2 h. The small resin sample was subjected to Sarin-Kaiser test for the completion of reaction. The resin was then filtered and washed with DMF (3×2 min), MeOH (2×2 min), dichloromethane (2×2 min) and DMF (2×2 min).

Step B. Synthesis of 2-[(1-Carboxamido-2-Tetrazoyl) Ethylcarbamoyl]-(D,L)-2-Aminotetraline Bound to Rink Amide Resin:

The compound obtained from step A was deprotected by removal of the Fmoc group with 20% piperidine in DMF for 30 min. Further resin washings were done with DMF (3×2 min), dichloromethane (DCM, 3×2 min), DMF (1×1 min). Then Fmoc-(D,L)-2-Aminotetraline-2-carboxylic acid (available from Acros) in DMF [10 mL, 2.0 mmol (4 equivalents with respect to the resin loading)], 2 mmol of HATU and 4 mmol of diisopropylethylamine (DIEA, 640 AL) were added to the resin to make a slurry. This slurry was stirred at room temperature for 2 h. The small resin sample was subjected to Sarin-Kaiser test for the completion of reaction. The resin was then filtered and washed with DMF (3×2 min), MeOH (2×2 min), dichloromethane (2×2 min) and DMF (2×2 min).

Step C. Synthesis of 2-[(1-Carboxamido-2-Terazolyl) Ethylcarbamoyl]-(D,L)-2-(2-Ethyl-n-Hexylamino)Tetraline Bound to Resin:

The Fmoc group on the aminotetraline nitrogen was removed by treatment with 20% piperidine in DMF for 30 min. The resin was then washed with DMF (3×2 min), dichloromethane (3×2 min), and DMF (1×1 min). Then a 0.2 M stock solution of 2-ethylhexanal (Aldrich Chemical Company, Milwaukee, USA) in 2% Acetic acid in trimethyl ortho formate (TMOF) (10 mL/g of resin) was added and the reaction was carried out for 2 h to form an imine derivative in situ. Then a 0.2 M stock solution of sodium cyanoborohydride (NaCNBH$_3$) in TMOF was added to the above reaction mixture to get the final concentration to 0.1 M and the reaction was continued at room temperature for 14 h. The resin was washed with TMOF (3×2 min), DMF (3×2 min), MeOH (3×2 min), dichloromethane (2×2 min) and dried under vacuum for 4 h.

Step D. Formation of 2-[(1-Carboxamido-2-Terazolyl) Ethylcarbamoyl]-(D,L)-2-(2-Ethyl-n-Hexylamino)Tetraline (Formula XXV):

Pre-cooled cleavage reagent (trifluoroacetic acid:dimethylsulfide:triisopropylsilane:H$_2$O; 90:2.5:2.5:5; v/v) was added (10 mL/g) to the dried resin and allowed to stir for 2 h at room temperature. The TFA cocktail was filtered into a 20 mL vial and TFA was evaporated on a rotavapor under vacuum. Diethyl ether was added to precipitate the compound along with trityl alcohol. The mixture was dissolved in 20% acetonitrile before purification on reverse phase HPLC.

Step E. Purification of compound XXV:

The crude compound from step D was dissolved in 10% aqueous acetonitrile and loaded onto the C18 column on Delta preparative HPLC. A linear gradient with 1% TFA acetonitrile and water was used as mobile phase. HPLC purity>95%; Mass (Perceptive Biosystem's Voyager-Maldi TOF): calculated for $C_{25}H_{37}N_5O_2$: 439.6; found: 440.6 (M+H).

Figure 5:
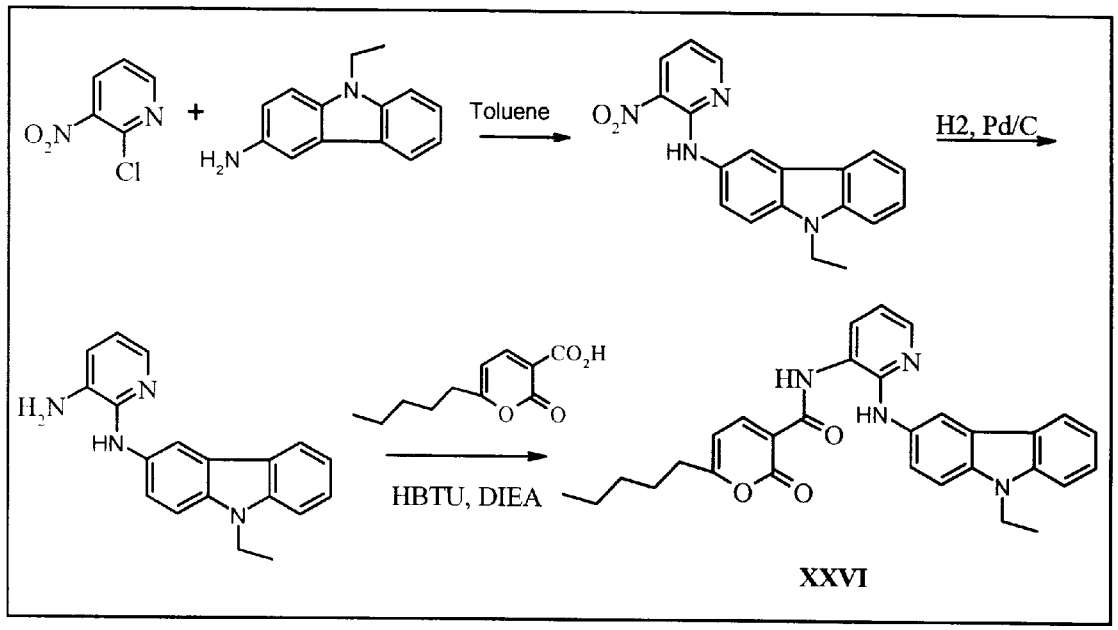
FIG. 5 depicts the scheme for the synthesis of the compound of Formula XXVI.

Example 5
Synthesis of 3-(9-Ethylcarbazolyl)Amino-Pyridin-2-yl-3-(2-Oxo-6-Pentyl-2H-Pyran-3-Carboxamide) (Formula XXVI) (FIG. 5; Scheme 5)

Step A. Synthesis of 2-[3-(9-Ethylcarbazolyl)Amino]-3-Nitropyridine:

To a solution of 2-chloro-3-nitropyridine (5 mmol, Aldrich Chemical Company, Milwaukee, USA) in toluene (10 mL) at ambient temperature were added 3-amino-9-ethylcarbazole (5 mmol, Aldrich Chemical Company, Milwaukee, USA). The mixture was heated to reflux for a period of 16 h. After cooling to room temperature, the mixture was diluted with ethyl acetate and washed successively with saturated sodium bicarbonate and brine. The organic layer was collected, dried over anhydrous sodium sulphate and concentrated in vacuo to give an oily product. This product was purified by chromatography over silica gel (eluent: 1:1 ethyl acetate:hexane) to give 2-[3-(9-ethylcarbazolyl)amino]-3-nitropyridine (68% yield); HPLC purity: >95%. This compound was then used in the next step.

Step B. Synthesis of 2-[3-(9-Ethylcarbazolyl)Amino]-3-Aminopyridine:

To a methanolic solution of 2-[3-(9-ethylcarbazolyl)] amino-3-nitropyridine obtained from step A were added 10% palladium over carbon (10% w/w), and the mixture was subjected to hydrogenation using a Parr hydrogenator at 40 psi for a period of 12 h. Then the slurry was filtered over Celite to remove the catalyst and the methanolic filtrate was evaporated to dryness to afford an oily product, 2-[3-(9-ethylcarbazolyl)amino]-3-aminopyridine. This was used as such in the next step.

Step C. Formation of 3-(9-Ethylcarbazolyl)Amino-Pyridin-2-yl-3-(2-Oxo-6-Pentyl-2H-Pyran-3-Carboxamide) (Formula XXVI):

To a solution of 2-oxo-6-pentyl-2H-pyran-3carboxylic acid (3 mM, Aldrich Chemical Company, Milwaukee, USA) in 10 mL dichloromethane at ambient temperature were added 2-1H-benzotriazol-1-yl)-1,1,3,3-tetramethyluronium hexafluorophosphate (HBTU; 3 mM; Advanced ChemTech, Louisville, USA) followed by 6 mM of diisopropylethylamine (DIEA; Aldrich Chemical Company, Milwaukee, USA). After 10 minutes, a solution of 3 mM of 2-[3-(9-ethylcarbazolyl)]amino-3-aminopyridine (obtained from step B) in 10 mL dichloromethane was added dropwise, and the resulting mixture was stirred at room temperature for 2 h. The crude product mixture was washed with brine, dried over anhydrous sodium sulphate and chromatographed over silica gel (eluent: 1:1 ethyl acetate:hexane to 100% ethyl acetate) to afford 71% of pure compound XXVI. HPLC purity>95%. %; Mass: calculated for $C_{30}H_{30}N_4O_3$: 495; found: 496 (M+H) (Finnigan LCQ).

Example 6

FSH Assay Method

General Overview

All compounds were stored in 96-well deepwell plates in DMSO at a nominal concentration of 10 mM (assuming perfect synthesis and yields). Compounds were screened for agonist activity at the FSH receptor using the recombinant FSH receptor stably transfected and expressed in Chinese Hamster Ovary cells (CHO cells) essentially as described in the work by Kelton, et al. (Molecular and Cellular Endocrinology, 1992, 89, 141–151). Since the FSH receptor is known to act via a G-protein (Gs) to activate adenylyl cyclase and hence raise intracellular levels of cAMP, the high throughput screening (HTS) assay used a gene reporter system consisting of the cAMP response element coupled upstream to the reporter gene, which in this case encoded the enzyme luciferase. An agonist at the FSH receptor increases cAMP in the cell, which results in activation of CREB (cAMP response element binding protein). This molecule interacts with the CRE element upstream of the gene and results in increased transcription of the genes downstream of the element. The substrate for luciferase (Packard Instrument Company, Meriden, Conn., USA) was added to the cells after appropriate incubation with the compounds of the invention or FSH (used as a positive control). The amount of luciferase expressed was measured by quantitating the luminescence produced by the enzyme using a TopCount scintillation/luminescence counter running in single photon counting mode. A compound that acts as an agonist at the receptor should produce light from the treated cells in proportion to its concentration within the incubation. Luminescence should be saturable at high concentrations of the compound.

HTS Primary Assay in Detail.

The compounds of the invention, in deepwell plates (Master plates) were loaded on the robotic deck along with the appropriate number of assay plates and daughter plates. A 10 µl aliquot from each master plate was transferred to the corresponding daughter plate and 90 µl of DME/F12 was added and mixed within each well. 20 µl was then removed from the daughter plate and dispensed into the assay plate. After addition of an aliquot of FSH (equivalent to an $EC_{100}$ response for this hormone [Final concentration of 5e-11 M]) to each of three wells on the plate, 80 pl of media (DME/F12+2% serum) and 100 µl aliquot of cells ($4 \times 10^5$/mL in the same media) were added and the plate incubated at 37° C. for 3 h 30 min. At this time the plate was removed from the incubator and media in each well was aspirated and the cells adhering to the bottom of the plate washed with 300 ill PBS containing 1 mM $Ca^{2+}$ and 1 mM $Mg^{2+}$. The PBS was aspirated and 100 µl PBS added to each well. 100 µl of Luclite (prepared as described by the manufacturer) was added to each well and the plate was shaken gently for 40 s prior to placement in the Topcount plate reader. After allowing 3.5 min for the plate to dark-adapt within the machine, the amount of luminescence generated was quantitated using Single Photon Counting mode. The data was transmitted electronically from the Topcount to the robot processing computer terminal and was renamed with an ID corresponding to the original master plate ID. Data were evaluated using an Excel macro and compounds showing activity comparable to that produced by an ECIOO of FSH itself were further analyzed in the same assay at differing concentrations. LDR (log-dose-response) curves were generated for these compounds in CHO cells containing the FSH receptor and these curves were also compared with those in either cells expressing a different Gs-linked receptor or in cells lacking any transfected receptor (to confirm receptor specificity).

Compounds that showed receptor specificity and activity at low concentrations were progressed to secondary assays that included dose-response curves in Y1 cells co-expressing the human FSH receptor or in isolated rat granulosa cells.

Figure 6:
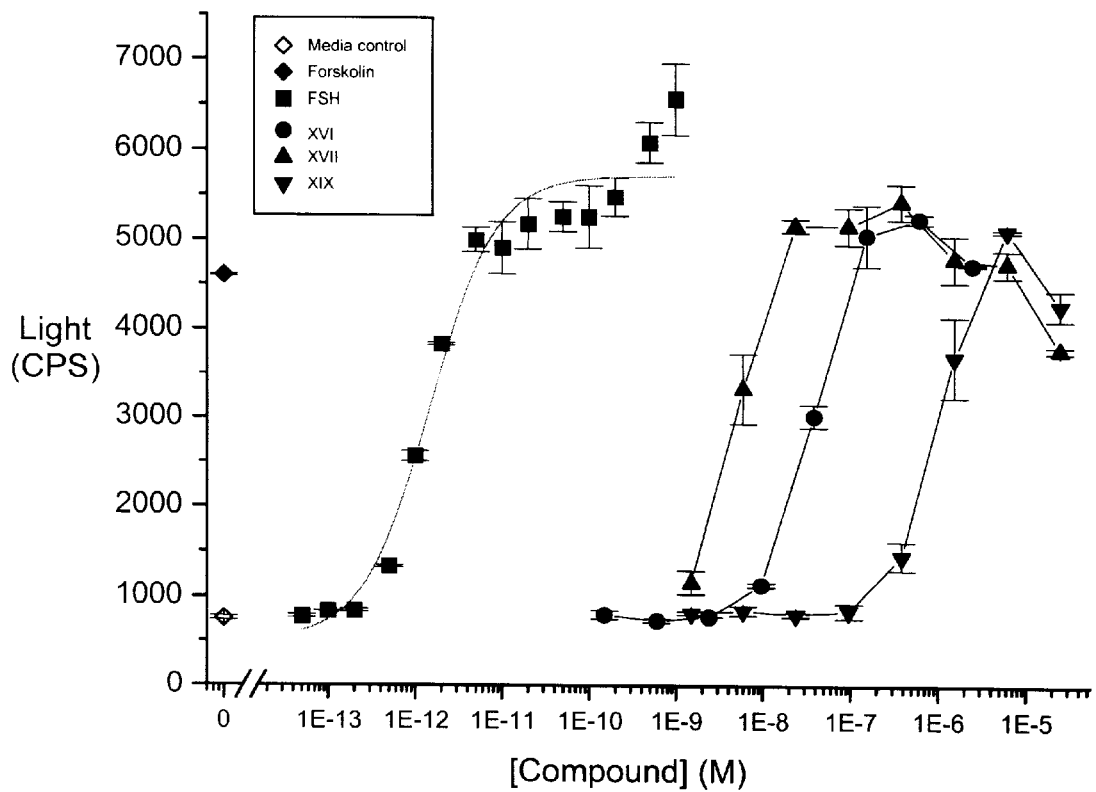
FIG. 6 displays the results of LDR analysis of compounds XVI, XVII, and XIX, compared to FSH.

FIG. 6 displays results of the FSH assay for compounds XVI, XVII and XIX. For comparison, results for FSH are also shown. Dose-response curves for each compound were generated and are displayed. From the graph, FSH has a $EC_{50}$ of 1.47 pM, compound XVI has a $EC_{50}$ of 38.8 nM, compound XVII has a $EC_{50}$ of 3.9 nM, and compound XIX has a $EC_{50}$ of 1.12 µM. A best-fit line is drawn for FSH. Results of the assay using media only and forskolin are also shown. The assay was performed using duplicate samples of each compound.

Example 7

Rat Granulosa Cell Assay

The primary rat granulosa cell bioassay for FSH was performed essentially as described (Dahl et al. (1989) *Methods Enzymol.*, 168: 414–423). Conversion of testosterone to estradiol in the presence of low nanomolar concentrations of FSH was detected using this assay. In this in vitro assay, conversion of androstendione to estrogen by granulosa cells in the presence of FSH was measured for compounds XVI and XVII. For comparison, FSH was also tested in the assay.

Cells were plated at 5000, 8000, 10,000 and 20,000 cells/well/200 µl of GAB medium on poly-D-lysine-coated 96-well tissue culture plates. Plates were incubated at 37° C. in a 5% $CO_2$/95% air incubator for 3 days. Cultures were washed prior to stimulation with FSH or LH. 50 µl of 4×concentrations of rhFSH, rhLH or forskolin was added to the cultures. To define the range of the dose response curve the rhFSH was diluted so that the final concentration on the cells was between $10^{-7}$ to $10^{-15}$ M with three doses per log at 1, 2 and 5. Forskolin was diluted so that the final concentration on the cells was 1 M. Cells were incubated@37° C. in 5% $CO_2$. Three days later, cell supernatants were collected and diluted 1:100 in GAB medium for measurement of estradiol by RIA. The RIA was performed according to manufacturer's directions except that an estradiol standard was prepared in absolute ethanol at 100 ng/mL and then further diluted in GAB medium, instead of kit buffer. The concentration of hormone was plotted on the X-axis against the amount of estradiol produced by the cells on the Y-axis using Origin graphics software.

Figure 7:
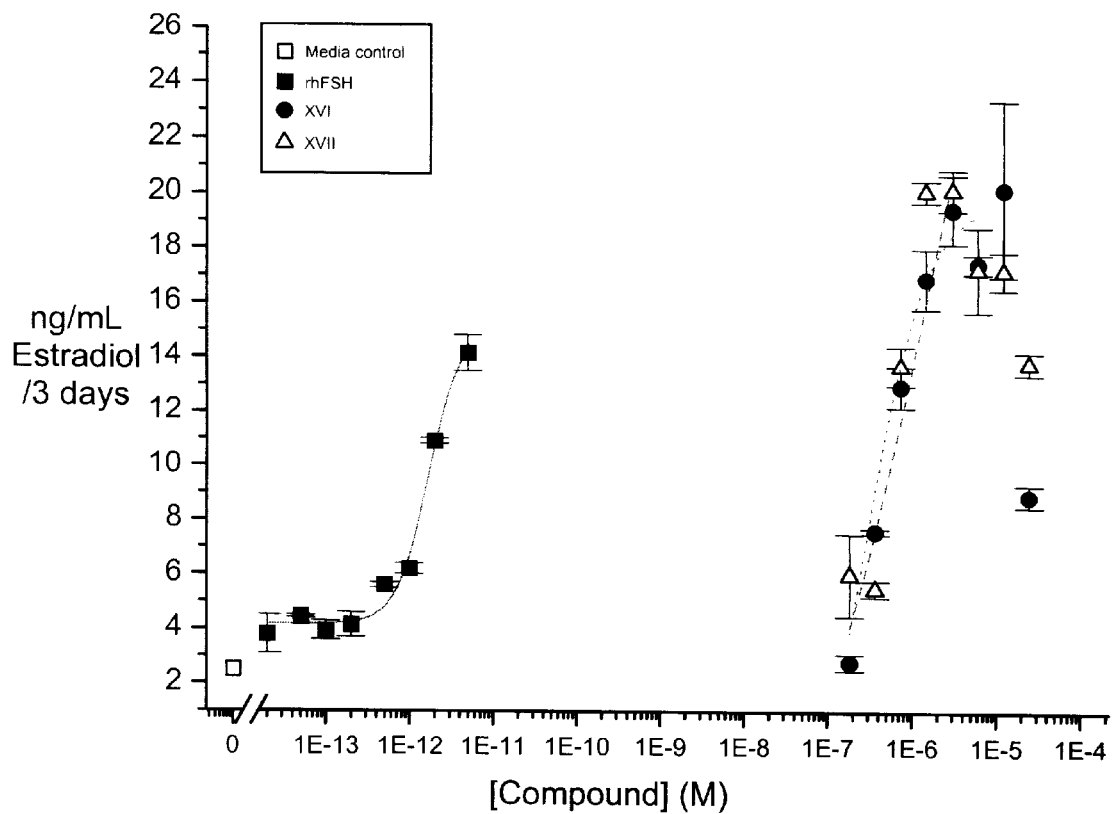
FIG. 7 displays the results of the primary rat granulosa cell bioassay for compounds XVI and XVII, compared to FSH.

As displayed in FIG. 7, compounds XVI and XVII show increasing estradiol production with increasing dose at concentrations between 200 nM and 5 µM. Above this concentration the compound showed a decrease in production-presumably since it caused a desensitization of the FSH receptors to further stimulation. The results show that compounds XVI and XVII stimulated estradiol production with $EC_{50}$ of 1.4 µM and 1.2 µM, respectively. Results of the assay using media only are also shown.

What is claimed is:

1. A compound of Formula XII,

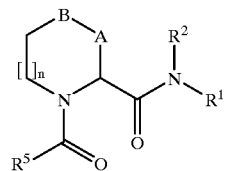

XII and pharmaceutically acceptable addition salts thereof, wherein n=0 or 1;

A and B are —CH$_2$— or —CH(R$^{10}$—, where R$^{10}$ is hydrogen, hydroxy, amino, amino substituted with one or more substituents, C$_1$–C$_6$ alkoxy, C$_1$–C$_6$ alkyl, C$_1$–C$_6$ alkyl substituted with one or more substituents, C$_1$–C$_6$ alkoxycarbonyl, cyano, C$_1$–C$_6$ aminoalkyl, or —(CH$_2$)$_s$NR$^6$R$^7$, where s is 1–6 and R$^6$ and R$^7$ are as defined below;

R$^1$ is carbazolyl or carbazolyl substituted with one or more substituents defined below;

R$^5$ is pyran, chromene, or benzofuran, or R$^5$ is pyran, chromene, or bensofuran substituted with one or more substituent's defined below;

R$^2$ is hydrogen, or straight or branched C$_1$–C$_6$ alkyl; and the substituents are independently (a) halogen, cyano, oxo, carboxy, formyl, nitro, amino, amidino, guanidino, C$_1$–C$_5$ alkyl or alkenyl or arylalkyl imino, carbamoyl, azido, carboxamido, mercapto, hydroxy, hydroxyalkyl, alkylaryl, arylalkyl, C$_1$–C$_8$ alkyl, C$_1$–C$_8$ alkenyl, C$_1$–C$_8$ alkoxy, C$_1$–C$_8$ alkoxycarbonyl, aryloxycarbonyl, C$_2$–C$_8$ acyl, C$_1$–C$_8$ alkylthio, arylalkylthio, arylthio, C$_1$–C$_8$ alkylsulfinyl, arylalkylsulfinyl, arylsulfinyl, C$_1$–C$_8$ alkylsulfonyl, arylalkylsulfonyl, arylsulfonyl, C$_1$–C$_6$ N-alkyl carbamoyl, C$_2$–C$_{15}$ N,N-dialkylcarbamoyl, C$_3$–C$_7$ cycloalkyl, aroyl, aryloxy, arylalkyl ether, aryl; or (b) NR$^6$R$^7$, where R$^6$ and R$^7$ are each independently hydrogen, cyano, oxo, carboxamido, amidino, C$_1$–C$_8$ hydroxyalkyl, C$_1$–C$_3$ alkylaryl, aryl-C$_1$–C$_3$ alkyl, C$_1$–C$_8$ alkyl, C$_1$–C$_8$ alkenyl, C$_1$–C$_8$ alkoxy, C$_1$–C$_8$ alkoxycarbonyl, aryloxycarbonyl, aryl-C$_1$–C$_3$ alkoxycarbonyl, C$_2$–C$_8$ acyl, C$_1$–C$_8$ alkylsulfonyl, arylalkylsulfonyl, arylsulfonyl, aroyl, aryl or (c) —(CH$_2$)$_s$NR$^6$R$^7$ where s is 1–6 and R$^6$ and R$^7$ are as defined in (b).

2. A compound according to claim 1 wherein R$^2$ is hydrogen and A and B are —(CH$_2$)—.

3. A compound according to claim 1, wherein the substituents are independently:

(a) halogen, C$_1$–C$_8$ alkyl, hydroxy, hydroxyalkyl, C$_1$–C$_8$ alkenyl, C$_1$–C$_8$ alkoxy, C$_1$–C$_8$ alkoxycarbonyl, aryloxycarbonyl, C$_2$–C$_8$ acyl, C$_1$–C$_8$ alkylthio, C$_1$–C$_8$ alkylsulfinyl, arylsulfinyl, C$_1$–C$_8$ alkylsulfonyl, C$_1$–C$_6$ N-alkyl carbamoyl, C$_2$–C$_{15}$ N,N-dialkylcarbamoyl, C$_3$–C$_7$ cycloalkyl; or (b) NR$^6$R$^7$ where R$^6$ and R$^7$ are each independently hydrogen, cyano, oxo, carboxamido, amidino, C$_1$–C$_8$ hydroxyalkyl, C$_1$–C$_8$ alkyl, C$_1$–C$_8$ alkenyl, C$_1$–C$_8$ alkoxy, C$_1$–C$_8$ alkoxycarbonyl, aryloxycarbonyl, aryl-C$_1$–C$_3$ alkoxycarbonyl, C$_2$–C$_8$ acyl, C$_1$–C$_8$ alkylsulfonyl, or (c) —(CH$_2$)$_s$NR$^6$R$^7$, where s is 1–6 and R$^6$ and R$^7$ are as defined in (b).

4. A compound of Formula IX,

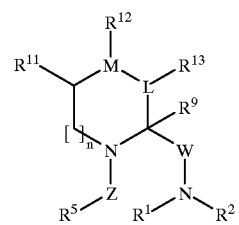

IX and pharmaceutically acceptable addition salts thereof, wherein n=0 or 1;

M and L are CH;

R$^9$, R$^{11}$, R$^{12}$ and R$^{13}$ are each independently hydrogen, halogen, cyano, oxo, carboxy, formyl, nitro, amino, amidino, guanidino, C$_1$–C$_5$ alkyl or alkenyl or arylalkyl imino, azido, mercapto, carboxamido, hydroxy, hydroxyalkyl, alkylaryl, arylalkyl, C$_1$–C$_8$ alkyl, C$_1$–C$_8$ alkenyl, C$_1$–C$_8$ alkoxy, C$_1$–C$_8$ C$_1$–C$_8$ alkoxycarbonyl, C$_2$–C$_8$ acyl, C$_1$–C$_8$ alkylthio, arylalkylthio, arylthio, C$_1$–C$_8$ alkylsulfinyl, arylalkylsulfinyl, arylsulfinyl, C$_1$–C$_8$ alkylsulfonyl, arylalkylsulfonyl, arylsulfonyl, C$_1$–C$_6$ N-alkyl carbamoyl, C$_2$–C$_{15}$ N,N-dialkylcarbamoyl, C$_1$–C$_5$ alkyl or alkenyl or arylalkyl ester, C$_1$–C$_7$ cycloalkyl, aroyl, aryloxy, benzyloxy, benzyloxy substituted with one or more substituents, aryl, or —NR$^6$R$^7$ or —(CH$_2$)$_s$NR$^6$R$^7$ where s is 1–6 and R$^6$ and R$^7$ are as defined in section (b) of the definition of substituent, below; or R$^9$, R$^{11}$, R$^{12}$, and R$^{13}$ each independently or in combination are a spiro or fused or bridged ring;

R$^1$ is carbazolyl or carbazolyl substituted with one or more substituents defined below:

R$^5$ is pyran, chromene, or benzofuran; or

R$^s$ is pyran, chromene, or benzofuran substituted with one or more substituents defined below;

R$^2$ is hydrogen, or straight or branched C$_1$–C$_6$ alkyl;

W is carbonyl (C═O);

Z is carbonyl (C═O); and the substituents are independently (a) halogen, cyano, oxo, carboxy, formyl, nitro, amino, amidino, guanidino, C$_1$–C$_5$ alkyl or alkenyl or arylalkyl imino, carbamoyl, azido, carboxamido, mercapto, hydroxy, hydroxyalkyl, alkylaryl, arylalkyl, C$_1$–C$_8$ alkyl, C$_1$–C$_8$ alkenyl, C$_1$–C$_8$ alkoxy, C$_1$–C$_8$ alkoxycarbonyl, aryloxycarbonyl, C$_2$–C$_8$ acyl, C$_1$–C$_8$ alkylthio, arylalkylthio, arylthio, C$_1$–C$_8$ alkylsulfinyl, arylalkylsulfinyl, arylsulfinyl, C$_1$–C$_8$ alkylsulfonyl, arylalkylsulfonyl, arylsulfonyl, C$_1$–C$_6$ N-alkyl carbamoyl, C$_2$–C$_{15}$ N,N-dialkylcarbamoyl, C$_3$–C$_7$ cycloalkyl, aroyl, aryloxy, arylalkyl ether, aryl; or (b) NR$^6$R$^7$, where R$^6$ and R$^7$ are each independently hydrogen, cyano, oxo, carboxamido, amidino, C$_1$–C$_8$ hydroxyalkyl, C$_1$–C$_3$ alkylaryl, aryl-C$_1$–C$_3$ alkyl, C$_1$–C$_8$ alkyl, C$_1$–C$_8$ alkenyl, C$_1$–C$_8$ alkoxy, C$_1$–C$_8$ alkoxycarbonyl, aryloxycarbonyl, aryl-C$_1$–C$_3$ alkoxycarbonyl, C$_2$–C$_8$ acyl, C$_1$–C$_8$ alkylsulfonyl, arylalkylsulfonyl, arylsulfonyl, aroyl, aryl; or (c) —(CH$_2$)$_s$NR$^6$R$^7$, where s is 1–6 and R$^6$ and R$^7$ are as defined in (b).

5. A compound according to claim 4 wherein
$R^9$, $R^{11}$, $R^{12}$, and $R^{13}$ are each independently hydrogen, halogen, cyano, oxo, carboxy, formyl, nitro, amino, amidino, guanidino, azido, mercapto, carboxamido, hydroxy, hydroxyalkyl, $C_1$–$C_8$ alkyl, $C_1$–$C_8$ alkenyl, $C_1$–$C_8$ alkoxy, $C_1$–$C_8$ alkoxycarbonyl, $C_2$–$C_8$ acyl, $C_1$–$C_8$ alkylthio, $C_1$–$C_8$ alkylsulfinyl, $C_1$–$C_8$ alkylsulfonyl, $C_1$–$C_6$ N-alkyl carbamoyl, $C_2$–$C_5$ N,N-dialkylcarbamoyl, $C_1$–$C_5$ alkyl or alkenyl ester, $C_1$–$C_7$ cycloalkyl, or —$NR^6R^7$ or —$(CH_2)_sNR^6R^7$ where s is 1–6; and the substituents are independently (a) halogen, $C_1$–$C_8$ alkyl, hydroxy, hydroxyalkyl, $C_1$–$C_8$ alkenyl, $C_1$–$C_8$ alkoxy, $C_1$–$C_8$ alkoxycarbonyl, aryloxycarbonyl, $C_2$–$C_8$ acyl, $C_1$–$C_8$ alkylthio, $C_1$–$C_8$ alkylsulfinyl, arylsulfinyl, $C_1$–$C_8$ alkylsulfonyl, $C_1$–$C_6$ N-alkyl carbamoyl, $C_2$–$C_{15}$ N,N-dialkylcarbamoyl, $C_3$–$C_7$ cycloalkyl; or (b) $NR^6R^7$, where $R^6$ and $R^7$ are each independently hydrogen, cyano, oxo, carboxamido, amidino, $C_1$–$C_8$ hydroxyalkyl, $C_1$–$C_8$ alkyl, $C_1$–$C_8$ alkenyl, $C_1$–$C_8$ alkoxy, $C_1$–$C_8$ alkoxycarbonyl, aryloxycarbonyl, aryl-$C_1$–$C_3$ alkoxycarbonyl, $C_2$–$C_8$ acyl, $C_1$–$C_8$ alkylsulfonyl; or (c) —$(CH_2)_sNR^6R^7$ where s is 1–6 and $R^6$ and $R^7$ are as defined in (b).

6. A compound selected from the group consisting of:

1-[(2-Oxo-6-pentyl-2H-pyran)-3-carbonyl]-3-hydroxypyrrolidine-2-carboxylic acid-3-(9-ethylcarbazolyl)amide;

1-[(2-Oxo-6-pentyl-2H-pyran)-3-carbonyl]-3-acetoxypyrrolidine-2-carboxylic acid-3-(9-ethylcarbazolyl)amide;

1-[(2-Oxo-6-isopropyl-2H-pyran)-3-carbonyl]-piperidine-2-carboxylic acid-3-(9-ethylcarbazolyl) amide;

1-[(2-Oxo-6-n-propyl-2H-pyran)-3-carbonyl]-piperidine-2-carboxylic acid-3-(9-ethylcarbazolyl)amide;

1-[(2-Oxo-6-pentyl-2H-pyran)-3-carbonyl]-piperidine-2-carboxylic acid-2-(3-indolyl)ethylamide;

1-[(2-Oxo-6-pentyl-2H-pyran)-3-carbonyl]-2-methylpyrrolidine-2-carboxylic acid-3-(9-ethylcarbazolyl) amide;

1-[(2-Oxo-6-pentyl-2H-pyran)-3-carbonyl]-4-hydroxypyrrolidine-2-carboxylic acid-3-(9-ethylcarbazolyl) amide;

1-[(2-Oxo-6-pentyl-2H-pyran)-3-carbonyl]-4-acetoxypyrrolidine-2-carboxylic acid-3-(9-ethylcarbazolyl) amide;

1-(Benzofuran-2-yl)carbonyl-pyrrolidine-2-carboxylic acid-3-(9-ethyl carbazolyl) amide;

1-[(2-Oxo-6-pentyl-2H-pyran)-3-carbonyl]4-oxopyrrolidine-2-carboxylic acid-3-(9-ethylcarbazolyl)amide;

1-[(2-Oxo-6-pentyl-2H-pyran)-3-carbonyl]3,4-dehydropyrrolidine-2-carboxylic-acid-3-(9-ethylcarbazolyl)amide;

1-(2-Oxo-2H-chromene-3-carbonyl)-pyrrolidine-2-carboxylic acid-3-(9-ethyl carbazolyl)amide; and 1-[(2-Oxo-6-pentyl-2H-pyran)-3-carbonyl]-2-[(9-ethylcarbazolyl)aminomethyl] pyrrolidine;

or a pharmaceutically acceptable addition salt thereof.

7. A compound selected from the group consisting of:

1-[(2-Oxo-6-pentyl-2H-pyran)-3-carbonyl]pyrrolidine-2-carboxylic acid-3-(9-ethylcarbazolyl)amide;

1-[(2-Oxo-6-pentyl-2H-pyran)-3-carbonyl]piperidine-2-carboxylic acid-3-(9-ethylcarbazolyl)amide; and 1-[(2-Oxo-6-pentyl-2H-pyran)-3-carbonyl]-4-hydroxypyrrolidine-2-carboxylic acid-3-(9-ethylcarbazolyl) amide or a pharmaceutically acceptable addition salt thereof.

8. A pharmaceutical composition comprising a compound according to any one of claims 1 to 7 and a pharmaceutically acceptable carrier, diluent or excipient thereof.

* * * * *